US012312601B2

(12) United States Patent
Kidoaki et al.

(10) Patent No.: US 12,312,601 B2
(45) Date of Patent: May 27, 2025

(54) CULTURE SUBSTRATE, METHOD FOR MANUFACTURING CULTURE SUBSTRATE, AND CULTURING METHOD AND CULTURING DEVICE FOR STEM CELL

(71) Applicant: Kyushu University, National University Corporation, Fukuoka (JP)

(72) Inventors: Satoru Kidoaki, Fukuoka (JP); Kousuke Moriyama, Fukuoka (JP); Hiroyuki Ebata, Fukuoka (JP)

(73) Assignee: Kyushu University, National University Corporation, Fukuoka (JP)

( * ) Notice: Subject to any disclaimer, the term of this patent is extended or adjusted under 35 U.S.C. 154(b) by 358 days.

(21) Appl. No.: 16/979,482

(22) PCT Filed: Mar. 11, 2019

(86) PCT No.: PCT/JP2019/009747
§ 371 (c)(1),
(2) Date: Sep. 9, 2020

(87) PCT Pub. No.: WO2019/176867
PCT Pub. Date: Sep. 19, 2019

(65) Prior Publication Data
US 2021/0062154 A1 Mar. 4, 2021

(30) Foreign Application Priority Data
Mar. 12, 2018 (JP) .................................. 2018-044437

(51) Int. Cl.
*C12N 5/0775* (2010.01)

(52) U.S. Cl.
CPC ........ *C12N 5/0662* (2013.01); *C12N 2531/00* (2013.01); *C12N 2533/54* (2013.01); *C12N 2535/00* (2013.01)

(58) Field of Classification Search
None
See application file for complete search history.

(56) References Cited

U.S. PATENT DOCUMENTS

| 2011/0189719 A1 | 8/2011 | Kuo et al. |
| 2015/0184122 A1 | 7/2015 | Le Berre et al. |
| 2015/0247126 A1 | 9/2015 | Kidoaki et al. |

FOREIGN PATENT DOCUMENTS

| CN | 102149811 A | 8/2011 |
| CN | 102472855 A | 5/2012 |

(Continued)

OTHER PUBLICATIONS

Engler et al. "Matrix Elasticity Directs Stem Cell Lineage Specification" (2006), Cell, vol. 126: 677-689. (Year: 2006).*

(Continued)

*Primary Examiner* — Teresa E Knight
(74) *Attorney, Agent, or Firm* — Morgan, Lewis & Bockius LLP

(57) ABSTRACT

The present disclosure provides a culture substrate for culturing stem cells, the culture substrate including a surface portion having: soft regions that extend side by side along a plurality of directions intersecting each other; and a plurality of stiff regions compartmented by the soft regions, wherein in the surface portion, the stiff regions have acute angle parts protruding toward the soft regions, and the cells can be deformed into a shape that is accommodated within the region of the stiff regions.

18 Claims, 19 Drawing Sheets

(56) References Cited

FOREIGN PATENT DOCUMENTS

| | | | |
|---|---|---|---|
| CN | 104024402 A | 9/2014 |
| CN | 106103700 A | 11/2016 |
| CN | 106459925 A | 2/2017 |
| JP | 2014-183770 A | 10/2014 |
| JP | 2015-163052 A | 9/2015 |
| JP | 2017-046592 A | 3/2017 |
| JP | 2017-055761 A | 3/2017 |
| WO | 2014/072177 A1 | 5/2014 |
| WO | 2017/006942 A1 | 1/2017 |

OTHER PUBLICATIONS

International Preliminary Report on Patentability and Written Opinion issued in corresponding International Patent Application No. PCT/JP2019/009747 dated Sep. 24, 2020.
Kawano et al., "Elasticity boundary conditions required for cell mechanotaxis on microelastically-patterned gels," Biomaterials, 32: 2725-2733 (2011).
Ueki et al., "Manipulation of cell mechanotaxis by designing curvature of the elasticity boundary on hydrogel matrix", Biomaterials, 41: 45-52 (2015).
Wenqiang Du, "Cell culture substrates patterned with anisotropic topography and stiffness and their applications in tissue engineering," University of Science and Technology of China: A dissertation for doctor's degree, Sep. 15, 2016, (2016) (see English abstract).
Kidoaki et al., "Rectified Cell Migration on Saw-Like Micro-Elastically Patterned Hydrogels with Asymmetric Gradient Ratchet Teeth," PLOS One, 8 (10): e78067 (2013).
Mahmud et al., "Directing cell motions on micropatterned ratchets," Nature Physics, 5 (8): 606-612 (2009).
Extended European Search Report issued in counterpart European Patent Application No. 19768235.4 dated Nov. 30, 2021.
McBeath et al., "Cell Shape, Cytoskeletal Tension, and RhoA Regulate Stem Cell Lineage Commitment," Developmental Cell, 6: 483-495 (2004).
Kidoaki et al., "Frustrated Differentiation of Mesenchymal Stem Cell Cultured on Microelastically-Patterned Photocurable Gelatinous Gels," Biophysical Journal, 102: 716a (2012).
Kidoaki et al., "Measurement of the Interaction Forces between Proteins and Iniferter-Based Graft-Polymerized Surfaces with an Atomic Force Microscope in Aqueous Media," Langmuir, 17: 1080-1087 (2001).
Idiris et al., "Force Measurement for Antigen-Antibody Interaction by Atomic Force Microscopy Using a Photograft-Polymer Spacer," Biomacromolecules, 6: 2776-2784 (2005).
Kidoaki et al., "Manipulation of Cell Movement by Designing Microelasticity Gradient Field of Cell Culture Substrate," Seibutsu Butsuri, 57 (3): 135-139 (2017) (see partial English translation).
Kidoaki et al., "Exercise culturing substrate which activates hepatocyte," Kyushu University, New Technology Presentation Meetings [online] Nov. 2018 (see partial English translation).
International Search Report issued in corresponding International Patent Application No. PCT/JP2019/009747 dated Jun. 4, 2019.

\* cited by examiner

Fig.11
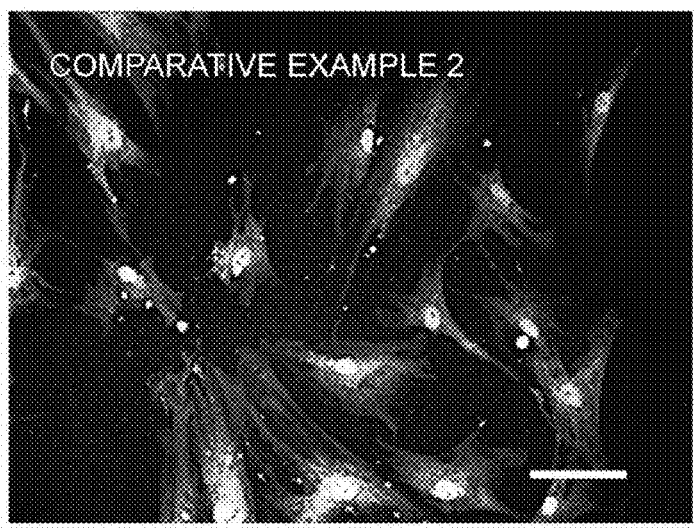
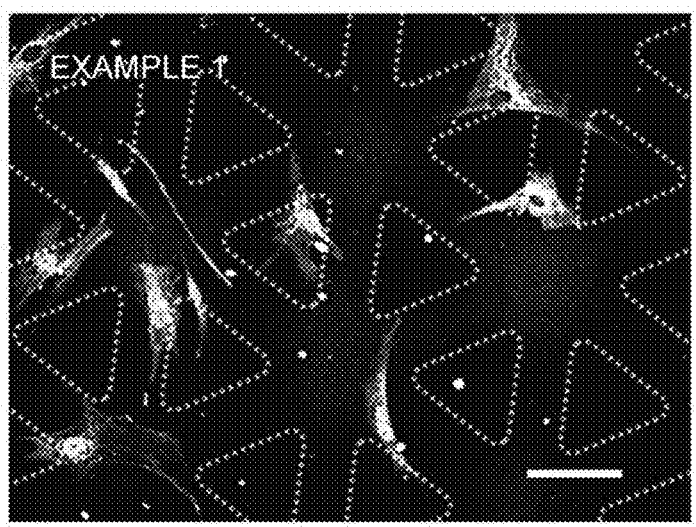
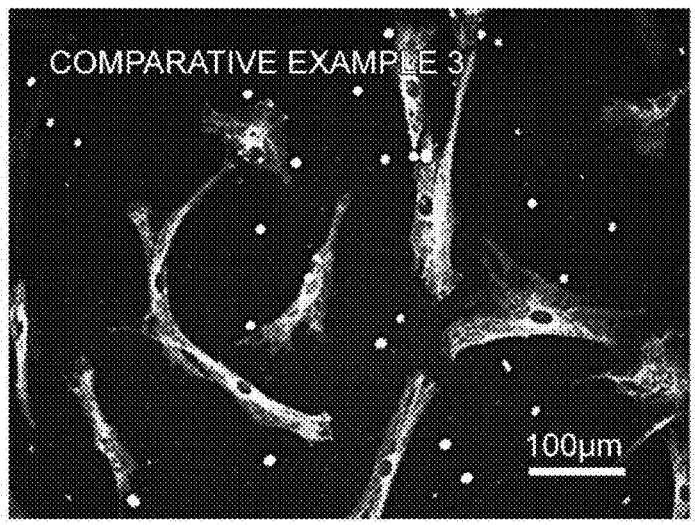

Fig.14
| BEFORE CULTURE | | AFTER 17 DAYS OF CULTURE | | | |
|---|---|---|---|---|---|
| CONTROL+ | CONTROL- | COMPARATIVE EXAMPLE 3 | COMPARATIVE EXAMPLE 2 | EXAMPLE 1 | REFERENCE EXAMPLE |
| 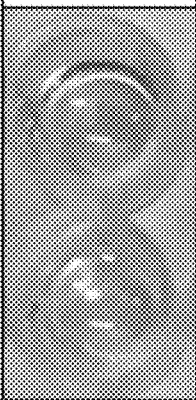 |  | 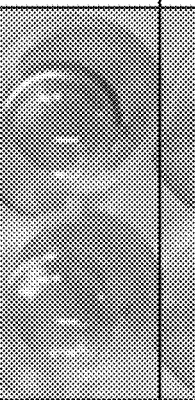 | 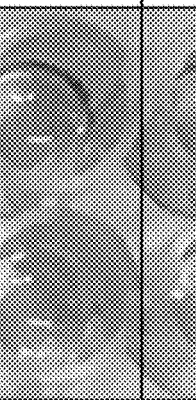 | 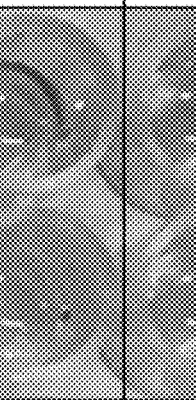 |  |

CULTURE SUBSTRATE, METHOD FOR MANUFACTURING CULTURE SUBSTRATE, AND CULTURING METHOD AND CULTURING DEVICE FOR STEM CELL

TECHNICAL FIELD

The present disclosure relates to a culture substrate, a method for manufacturing a culture substrate, a method for culturing stem cells, and a culturing device.

BACKGROUND ART

The process for determining the differentiation lineage of stem cells is affected by a variety of factors. For example, it is known that spreading of stem cells on a substrate during culture affects the determination of the differentiation lineage (for example, Non Patent Literature 1), that the determination is affected by the external stimulation that stem cells receive during culture (stimulation that cells receive due to the differences in the chemical characteristics, mechanical characteristics, and the like of the culture substrate surface), and the like. In the case of culturing stem cells on a Petri dish, since the stem cells continuously receive a constant drag force from the Petri dish, the differentiation lineage may be determined in accordance with the force of the stimulation.

In recent years, substrates and culturing methods for culturing stem cells in an undifferentiated state have been investigated. For example, in Patent Literature 1, a method for culturing artificial pluripotent stem cells by using a cell culture substrate formed by immobilizing a cell-adhesive protein on the surface of an elasticity-variable gel, wherein the elasticity-variable gel has an elastic modulus of higher than 1 kPa and lower than 100 MPa, is disclosed.

Furthermore, a method for culturing stem cells on a culture substrate on which a striped pattern having stiff regions and soft regions is provided has been investigated. It has been expected that as stem cells freely run so as to travel across the stiff regions and the soft regions on the substrate, the stimulation that the stem cells receive from the substrate is varied, and thereby the determination of the differentiation lineage is inhibited (for example, Non Patent Literature 2 and the like).

CITATION LIST

Patent Literature

Patent Literature 1: Japanese Unexamined Patent Publication No. 2015-163052

Non Patent Literature

Non Patent Literature 1: Rowena McBeath, et al., "Cell Shape, Cytoskeletal Tension, and RhoA Regulate Stem Cell Lineage Commitment," Development Cell, 2004, 6, p. 483-495

Non Patent Literature 2: Satoru Kidoaki, Shuhei Jinnouchi, "Frustrated Differentiation of Mesenchymal Stem Cell Cultured on Microelastically-Patterned Photocurable Gelatinous Gels," Biophysical Journal, 2012, 102, p. 716a Non Patent Literature 3: Satoru Kidoaki, et al., "Measurement of the Interaction Forces between Proteins and Iniferter-Based Graft-Polymerized Surfaces with an Atomic Force Microscope in Aqueous Media," Langmuir 2001, 17, p. 1080-1087

Non Patent Literature 4: Alimjan Idiris, Satoru Kidoaki, et al., "Force Measurement for Antigen-Antibody Interaction by Atomic Force Microscopy Using a Photograft-Polymer Spacer," Biomacromolecules, 2005, 6, p. 2776-2784

SUMMARY OF INVENTION

Technical Problem

However, even in a case in which stem cells are cultured on a culture substrate provided with a striped pattern such as described above, a bias occurs in the movement of stem cells, such as that the stem cells move only over one region of the stiff regions or the soft regions on the substrate. Due to this bias in movement, it may be difficult to culture stem cells while sufficiently maintaining an undifferentiated state of the stem cells. It is considered that it will be useful to have a culture substrate in which cells move isotropically over the substrate such that the stem cells during culture repeatedly move among different regions.

It is an object of the present disclosure to provide a culture substrate with which the direction of movement of stem cells on the substrate surface may be made isotropic, a method for manufacturing a culture substrate, and a method for culturing stem cells.

Solution to Problem

An aspect of the present disclosure provides a culture substrate for culturing stem cells, the culture substrate comprising a surface portion having: soft regions that extend side by side along a plurality of directions intersecting each other; and a plurality of stiff regions compartmented by the soft regions, wherein in the surface portion, the stiff regions have acute angle parts protruding toward the soft regions, and the stem cells can be deformed into a shape that is accommodated within the region of the stiff regions.

Through the investigation of the inventors, it has been found that in a case where a conventional culture substrate in which two kinds of regions, namely, stiff regions and soft regions, are formed in a striped pattern on the surface of the substrate is used, the proportion of stem cells moving along the stiff regions in the middle of culture is large. This is speculated to be related to the fact that cells have cytotaxis of preferably moving over a stiff region (positive durotaxis). That is, it has been newly found that in the case of using a conventional culture substrate, there is a tendency that stem cells exhibit less movement of coming and going over between soft regions and stiff regions, and the external stimulation that the stem cells receive is likely to become a single stimulation.

Since the above-described culture substrate has soft regions and stiff regions on the surface, and the stiff regions are compartmented by the soft regions, the stem cells selectively moving only over the stiff regions during culture may be suppressed. Furthermore, as the stiff regions have acute angle parts protruding toward the soft regions on the surface of the culture substrate, negative durotaxis in which cells move from stiff regions to soft regions may be induced in those portions. As a result of these actions, it is possible to suppress a bias in the movement of stem cells (stem cells preferably moving over stiff regions) on the surface of a culture substrate. By causing the stem cells to move over stiff regions and soft regions, the mechanical stimulation sensed by the stem cells may be varied at a high frequency over the culturing period.

According to an aspect of the present disclosure, there is provided a culture substrate for culturing stem cells, the culture substrate comprising a surface portion having: soft regions that extend side by side along a plurality of directions intersecting each other; and a plurality of stiff regions compartmented by the soft regions and having a higher compressive modulus of elasticity than the soft regions, wherein in the surface portion, the stiff regions have acute angle parts protruding toward the soft regions, and the stem cells can be deformed into a shape that is accommodated within the region of the stiff regions.

Since the culture substrate comprises a surface having regions with different compressive moduli of elasticity, and stiff regions having a high compressive modulus of elasticity are compartmented by soft regions, cells to be cultured selectively moving only over the stiff regions may be suppressed. Furthermore, as the stiff regions have acute angle parts protruding toward the soft regions on the surface of the culture substrate, negative durotaxis in which cells move from the stiff regions to the soft regions may be induced in the portions. As a result of these actions, it is possible to suppress a bias in the movement of stem cells (stem cells preferably moving over stiff regions) on the surface of the culture substrate, and by causing the stem cells to move over stiff regions and soft regions, the mechanical stimulation sensed by the stem cells may be varied at a high frequency over the culturing period. Therefore, by culturing stem cells using the above-described culture substrate, the culturing history being accumulated in the stem cells may be suppressed, and stem cells may be cultured while sufficiently maintaining an undifferentiated state.

The above-described acute angle parts exhibit a chamfering shape, and the radius of curvature thereof may be 50 µm or less. When the radius of curvature of the acute angle parts is in the above-described range, the movement of stem cells from the stiff regions to the soft regions may be further promoted, and the movement of stem cells over the culture substrate may be made more isotropic.

At least one of the plurality of stiff regions may have a triangular shape. As at least one of the stiff regions has a triangular shape, the frequency of movement of the stem cells from the stiff regions to the soft regions in the acute angle parts (corresponding to the vicinity of apexes of a triangle) present in the stiff regions, and the frequency of movement of the stem cells from the soft regions to the stiff regions in flat parts (corresponding to the vicinity of edges of a triangle) of the stiff regions may be made equal.

The area of each of the stiff regions may be 5,000 to 13,000 µm$^2$. By adjusting the area of the stiff region to the above-described range, a culture substrate that may cope with various sizes of stem cells may be prepared. By adjusting the area of the stiff region to the above-described range, the bias between the proportion of movement of stem cells over the stiff regions and the proportion of movement of stem cells over the soft regions may be further reduced.

The compressive modulus of elasticity of the stiff regions may be 10 or more times the compressive modulus of elasticity of the soft regions. By adjusting the compressive modulus of elasticity of the stiff region to the above-described range, a culture substrate in which stem cells may recognize the difference between the stimulation from the stiff region and the stimulation from the soft region, and with which it is possible to further inhibit the determination of the differentiation lineage (hereinafter, may also be referred to as differentiation bias), may be obtained.

The compressive modulus of elasticity of the stiff regions may be 30 kPa or higher. Migration of transcriptional coactivators, which are involved in the determination of the differentiation lineage of stem cells, into the cell nucleus may be caused by the stimulation that stem cells receive from the substrate. When the compressive modulus of elasticity of the stiff region is in the above-described range, on the stiff region, transient migration of various transcriptional coactivators into the cell nucleus may be further promoted. Since the migration of the transcriptional coactivators into the cell nucleus is not promoted on the soft region, the reactions in the stem cells, that is, the nuclear gene metabolic reactions promoted by transcriptional coactivators, occurring on the stiff regions and on the soft regions are qualitatively and quantitatively different from each other. By adjusting the compressive modulus of elasticity of the stiff region to the above-described range, the stimulation exerted from each of the stiff regions and the soft regions to the stem cells may be adjusted, and the intracellular biological reactions concomitant with the stimulation may be converted to biological reactions having clearly different properties. That is, by adjusting the compressive modulus of elasticity of the stiff region to the above-described range, the differentiation bias of stem cells to a specific direction may be more sufficiently prevented.

The soft region may include a photopolymerizable compound, and the photopolymerizable compound may include a photocurable styrenated gelatin.

According to an aspect of the present disclosure, there is provided a culture substrate for culturing stem cells, the culture substrate comprising a surface portion having: soft regions that extend side by side along a plurality of directions intersecting each other; and a plurality of stiff regions compartmented by the soft regions and having a higher coefficient of viscosity than the soft regions, wherein in the surface portion, the stiff regions have acute angle parts protruding toward the soft regions, and the stem cells can be deformed into a shape that is accommodated within the region of the stiff regions.

Since the culture substrate comprises a surface having regions with different coefficients of viscosity, and the stiff regions having a high coefficient of viscosity are compartmented by the soft regions, the cells to be cultured selectively moving only over the stiff regions may be suppressed. Furthermore, as the stiff regions have acute angle parts protruding toward the soft regions on the surface of the culture substrate, negative durotaxis in which cells move from the stiff regions to the soft regions may be induced in these portions. As a result of these actions, it is possible to suppress a bias in the movement of stem cells (stem cells preferably moving over stiff regions) on the surface of the culture substrate, and by causing the stem cells to move over stiff regions and soft regions, the mechanical stimulation sensed by the stem cells may be varied at a high frequency over the culturing period. Therefore, by culturing stem cells using the above-described culture substrate, the culturing history being accumulated in the stem cells may be suppressed, and stem cells may be cultured while sufficiently maintaining an undifferentiated state.

The acute angle parts exhibit a chamfering shape, and the radius of curvature thereof may be 50 µm or less. When the radius of curvature of the acute angle parts is in the above-described range, the movement of stem cells from the stiff regions to the soft regions may be further promoted, and the movement of stem cells over the culture substrate may be made more isotropic.

At least one of the plurality of stiff regions may have a triangular shape. As at least one of the stiff regions has a triangular shape, the frequency of movement of the stem cells from the stiff regions to the soft regions in the acute angle parts (corresponding to the vicinity of apexes of a triangle) present in the stiff regions, and the frequency of movement of the stem cells from the soft regions to the stiff regions in flat parts (corresponding to the vicinity of edges of a triangle) of the stiff regions may be made equal.

The area of each of the stiff regions may be 5,000 to 13,000 μm². By adjusting the area of the stiff region to the above-described range, a culture substrate that may cope with various sizes of stem cells may be prepared. By adjusting the area of the stiff region to the above-described range, the bias between the proportion of movement of stem cells over the stiff regions and the proportion of movement of stem cells over the soft regions may be further reduced.

According to an aspect of the present disclosure, there is provided a method for manufacturing a culture substrate, the method having: forming a composition layer including a photopolymerizable compound and a photopolymerization initiator, on a support; and irradiating the composition layer with light in a patternwise fashion and thereby obtaining the above-mentioned culture substrate.

In the method for manufacturing a culture substrate, regions having different compressive moduli of elasticity are formed on the surface of the culture substrate by irradiating the composition layer with light in a patternwise fashion. At this time, the above-mentioned culture substrate may be produced by controlling the light-irradiated regions such that stiff regions having a high compressive modulus of elasticity are compartmented by soft regions, and such that the stiff regions have acute angle parts protruding toward the soft regions on the surface of the culture substrate. The culture substrate to be produced comprises the features of the above-mentioned culture substrate, and as a result of the actions, it is possible to suppress a bias in the movement of stem cells (stem cells preferably moving over stiff regions) on the surface of the culture substrate. Therefore, the method for manufacturing a culture substrate may provide a substrate that suppresses the culturing history being accumulated in the stem cells and is capable of culturing stem cells while sufficiently maintaining an undifferentiated state.

The photopolymerizable compound may include a photocurable styrenated gelatin.

According to an aspect of the present disclosure, there is provided a method for culturing stem cells, the method including, culturing stem cells on the above-mentioned culture substrate.

The method for culturing stem cells may culture stem cells while sufficiently maintaining an undifferentiated state, even without using an unknown and undefined differentiation inhibitory factor that is prepared and supplied from animal blood serum or the like, by using the above-mentioned culture substrate. In the case of mesenchymal stem cells, a differentiation inhibitory factor that effectively suppresses differentiation and a differentiation and proliferation factor related to the maintenance of undifferentiability and pluripotency have not been established. Conventionally, with regard to the culture of stem cells using a conventional cell culture dish and a standard medium, it has been implemented to select and add a factor that is considered to be effective for the sustentation of stem cells at every time of culturing. With regard to the method for culturing stem cells, it is not necessary to select and use components derived from animal blood serum and the like, and it is also possible to avoid the stimulation from the substrate being accumulated in the stem cells during culture. Therefore, the quality, safety, and the like of proliferated stem cells thus obtained may be enhanced. Since the stem cells cultured by the method for culturing stem cells according to the present embodiment may be of stable quality while maintaining an undifferentiated state, the stem cells may be useful as stem cells for research and regenerative medicine.

According to an aspect of the present disclosure, there is provided a culturing device having stem cells and a culture substrate for culturing the stem cells, the culture substrate comprising a surface portion having: soft regions that extend side by side along a plurality of directions intersecting each other; and a plurality of stiff regions compartmented by the soft regions, wherein in the surface portion, the stiff regions have acute angle parts protruding toward the soft regions, and the stem cells can be deformed into a shape that is accommodated within the region of the stiff regions.

Since the above-described culture substrate has soft regions and stiff regions on the surface, and the stiff regions are compartmented by the soft regions, stem cells selectively moving only over the stiff regions during culture may be suppressed. Furthermore, as the stiff regions have acute angle parts protruding toward the soft regions on the surface of the culture substrate, negative durotaxis in which cells move from the stiff regions to the soft regions may be induced in these portions. As a result of these actions, it is possible to suppress a bias in the movement of stem cells (stem cells preferably moving over stiff regions) on the surface of a culture substrate. By causing the stem cells to move over stiff regions and soft regions, the mechanical stimulation sensed by the stem cells may be varied at a high frequency over the culturing period.

The stiff regions may have a higher compressive modulus of elasticity than the soft regions. By having the compressive moduli of elasticity at the stiff regions and the soft regions defined by the relationship such as described above, the difference between the stimulation from the stiff regions and the stimulation from the soft regions may be made more easily recognizable by stem cells.

The stiff regions may have a higher coefficient of viscosity than the soft regions. By having the coefficients of viscosity at the stiff regions and the soft regions defined by the relationship such as described above, the difference between the stimulation from the stiff regions and the stimulation from the soft regions may be made more easily recognizable by stem cells.

Advantageous Effects of Invention

According to the present disclosure, a culture substrate with which the direction of movement of stem cells on the substrate surface may be made isotropic, a method for manufacturing a culture substrate, and a method for culturing stem cells may be provided.

In conventional substrates, in a case in which a substrate has soft regions and stiff regions on the surface (also referred to as having non-uniform soft and stiff compartments), a bias is caused in the direction of movement of the stem cells to be cultured. In contrast, according to the present disclosure, a culture substrate that has non-uniform soft and stiff compartments and may make the movement of stem cells to be cultured on that surface isotropic, a method for manufacturing a culture substrate, and a method for culturing stem cells, may be provided.

BRIEF DESCRIPTION OF DRAWINGS

FIG. 11 is a diagram showing a fluorescence microscopic photograph showing the localization of YAP inside stem cells on a culture substrate.

FIG. 14 is a diagram showing the results of subjecting stem cells that have been collected after culture to the induction of differentiation.

DESCRIPTION OF EMBODIMENTS

Figure 1:
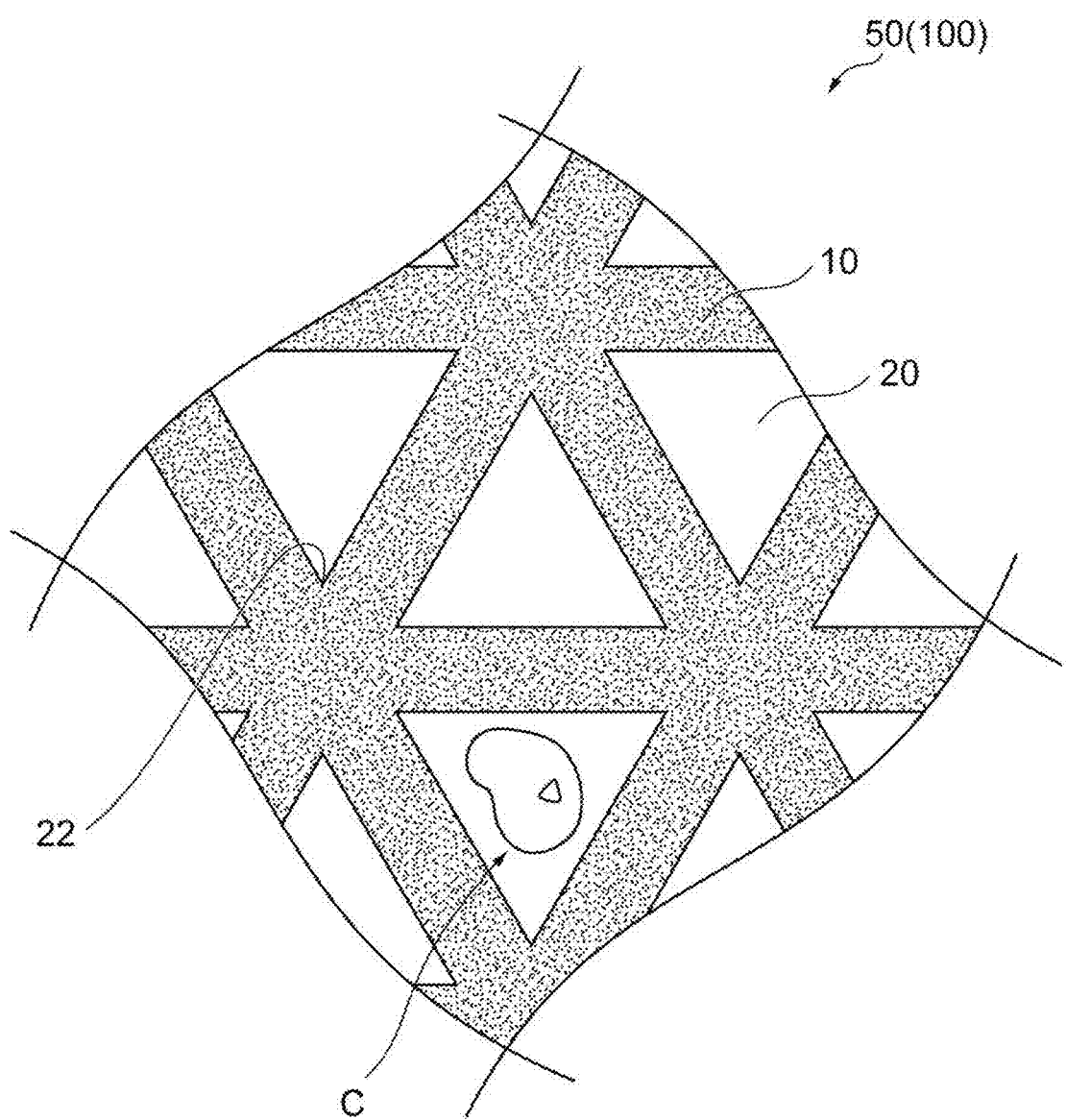
FIG. 1 is a schematic diagram illustrating a portion of an embodiment of a culture substrate.

In the following description, embodiments of the present disclosure will be described, with reference to the drawings depending on cases. However, the following embodiments are merely examples for explaining the present disclosure and are not intended to limit the present disclosure to the following contents. Unless particularly stated otherwise, the positional relationship such as top, bottom, right, and left are based on the positional relationships shown in the drawings. The dimensional ratio of each element is not limited to the ratios illustrated in the drawings.

<Culture Substrate>

An embodiment of the culture substrate is a culture substrate for culturing stem cells and comprises a surface portion having: soft regions that extend side by side along a plurality of directions intersecting each other; and a plurality of stiff regions compartmented by the soft regions. In the surface portion, the stiff regions have acute angle parts protruding toward the soft regions, and the stem cells can be deformed into a shape that is accommodated within the region of the stiff regions.

FIG. 1 is a schematic diagram illustrating a portion of an embodiment of the culture substrate. The culture substrate 100 shown in FIG. 1 comprises a surface 50 having: soft regions 10 that extend side by side along a plurality of directions intersecting each other; and a plurality of stiff regions 20 compartmented by the soft regions 10. In the surface 50, the stiff regions 20 have acute angle parts 22 protruding toward the soft regions 10. In FIG. 1, a state in which stem cells C are accommodated within the region of the stiff regions 20 is shown. That is, it is shown that the area of the stiff regions 20 is an area in which stem cells C can be accommodated.

The stiff regions 20 may have a higher compressive modulus of elasticity than the soft regions 10. As the surface 50 of the culture substrate 100 comprises a plurality of regions having different compressive moduli of elasticity, it is possible to change the stimulation that the cultured cells receive when the cells move over the plurality of above-described regions. That is, the mechanical stimulation sensed by the cells that are cultured on the culture substrate 100 can be varied at a high frequency over the culturing period. The compressive modulus of elasticity of the stiff regions 20 may be 10 or more times, 12 or more times, or 15 or more times, the compressive modulus of elasticity of the soft regions 10. The compressive modulus of elasticity of the stiff regions 20 may be 30 or less times, or 20 or less times, the compressive modulus of elasticity of the soft regions 10. By adjusting the compressive modulus of elasticity of the stiff regions 20 to the above-described range, the difference between the stimulation from the stiff regions 20 and the stimulation from the soft regions 10 can be made more recognizable by stem cells. By varying the stimulation that stem cells receive at a high frequency over the culturing period, the undifferentiated state of the stem cells can be maintained more sufficiently.

The compressive moduli of elasticity of the stiff regions 20 and the soft regions 10 can be determined, for example, as follows. For example, explanation will be given by assuming the culture of human mesenchymal stem cells (hMSC). In the case of hMSC, the respective appropriate compressive moduli of elasticity of the stiff regions 20 and the soft regions 10 may be determined by utilizing the fact that the migration of YAP to the cell nucleus is affected by the stimulation that hMSC receives from the substrate. That is, the respective appropriate compressive moduli of elasticity of the stiff regions 20 and the soft regions 10 in the culture substrate for culturing hMSC can be determined by observing the intracellular behavior of transcriptional coactivator YAP, which is known to be involved in the determination of the differentiation lineage of hMSC. First, a plurality of culture substrates having different compressive moduli of elasticity is prepared, culture of hMSC is carried out on each of the culture substrates, and the sites where YAP is localized within cells are specified. By performing such an observation, the threshold value of the compressive modulus of elasticity of the substrate in relation to whether YAP will migrate to the cell nucleus or remain in the cytoplasm, is determined. Then, the compressive modulus of elasticity of the stiff regions 20 and the compressive modulus of elasticity of the soft regions 10 can be determined so as to exceed the determined threshold value. In the above-described example, the compressive moduli of elasticity of the stiff regions 20 and the soft regions 10 are determined on the basis of the intracellular behavior of YAP; however, attention may also be paid to other factors, depending on the target stem cells or the like. As the other factors, proteins known to be such that migration thereof to the cell nucleus is affected in accordance with the stiffness of the substrate, and the like can be employed, and examples include TAZ, RUNX2, and the like.

The compressive modulus of elasticity of the stiff regions 20 can be adjusted depending on the type of the stem cells as the object of culture, the stage of differentiation, and the like. The compressive modulus of elasticity of the stiff regions 20 may be, for example 30 kPa or higher, 40 kPa or higher, or 50 kPa or higher, and may be 100 kPa or lower. The compressive modulus of elasticity of the soft regions 10 may be, for example, lower than 30 kPa, 20 kPa or lower, or 10 kPa or lower, and may be 5 kPa or higher. According to the present specification, the compressive modulus of elasticity means the compressive modulus of elasticity of the substrate surface, which is measured using an atomic force microscope (AFM), and is the compressive modulus of elasticity measured when a cantilever of the AFM is pushed into the substrate surface, and the substrate is compressed.

The stiff regions 20 are compartmented into a plurality of regions by the soft regions 10 on the surface 50 of the culture substrate 100. The stiff regions 20 have acute angle parts 22 protruding toward the soft regions 10. The acute angle parts 22 of the stiff regions 20 may exhibit a chamfering shape. The radius of curvature at the acute angle parts 22 exhibiting a chamfering shape may be, for example, 50 µm or less, 45 µm or less, or 40 µm or less. The shape of the stiff regions 20 may be, for example, a triangular shape, a parallelogram shape, a rhombic shape, a star shape, and the like, and at least one of the stiff regions compartmented into a plurality of regions may have a triangular shape.

The length of one side of the stiff region 20 may be, for example, 100 µm or more, 130 µm or more, or 150 µm or more, and may be 300 µm or less, or 250 µm or less. In stiff regions 20 that are adjacent to each other, the distance between the acute angle parts 22 (for example, in the case of a triangular shape, the distance between the apexes of two triangular-shaped regions facing each other) may be, for example, 200 µm or less, 150 µm or less, or 120 µm or less, and may be 80 µm or more or 100 µm or more.

The shape of the stem cells C is not constant and can be deformed. In a case in which the stem cells have, for example, a shape that is not accommodated within the region of the stiff regions but spans a plurality of stiff regions and soft regions, the stimulations that the stem cells receive from the stiff regions and the soft regions of the substrate are averaged, and the situation becomes similar to receiving a constant stimulation. Therefore, in a case in which the stem cells cannot be deformed into a shape that is accommodated within the region of the stiff regions, it is difficult to vary the stimulation that the stem cells receive, at a high frequency over the culturing period. The culture substrate 100 is used for the culture of stem cells that can be deformed so as to acquire a size that can be accommodated within the region of the stiff regions 20. In other words, the area of the stiff regions 20 in the culture substrate 100 may be adjusted according to the size of the target stem cells C to be cultured, or may be adjusted such that at least one embodiment obtained when the stem cells C have been deformed fits in the area of the stiff regions 20. The shape (area) of the stem cells C is, for example, in the range of 13,000 µm$^2$ or less and can be checked by an observation made using optical microscopic observation or the like.

The area of the stiff regions 20 may be 5,000 to 13,000 µm$^2$ or may be 5,000 to 10,000 µm$^2$. By adjusting the area of the stiff regions 20 to the above-described range, a culture substrate that can cope with various sizes of stem cells can be prepared. The area of the stiff regions 20 can be checked by an observation made using optical microscopic observation or the like.

The surface 50 of the culture substrate 100 may include, for example, a composition containing a polymer compound, or a processed product (for example, a cured product) of the composition, or may include the polymer compound or a processed product thereof. Examples of the polymer compound include a naturally occurring polymer, a synthetic polymer, and the like. Regarding the polymer compound, a plurality of polymers may be used in combination. Regarding the form of the polymer compound or a processed product thereof, a polymer gel, a polymer concentrated solution sol, an elastomer, nanomicrofibers, a nonwoven fabric, and the like may be mentioned. For the surface 50 of the culture substrate 100, polymer compounds in a plurality of forms and the like may be used in combination. Furthermore, the culture substrate 100 may be formed of the above-mentioned composition containing a polymer compound, or a processed product (for example, a cured product) of the composition.

Examples of the naturally occurring polymer include biologically derived biopolymers such as collagen, gelatin, chitin, chitosan, alginic acid, and hyaluronic acid; and the like. The synthetic polymer may be a homopolymer or may be a copolymer. Examples of the copolymer include a random copolymer, an alternating copolymer, a block copolymer, a graft copolymer, and the like. Specific examples of the synthetic polymer include synthetic polymers such as polyacrylamide, polyethylene glycol diacrylate, polydimethylsiloxane, a segmented polyurethane, a fluorine-containing segmented polyurethane, polydimethylsiloxane, a polydimethylsiloxane-polycarbonate block copolymer, a fully saponified polyvinyl alcoholic hydrated rubber, isoprene rubber, butadiene rubber, ethylene-propylene rubber, styrene-butadiene rubber, acrylonitrile-butadiene rubber, and a styrene-butadiene-styrene block copolymer; and the like. As the polymer compound, for example, modified products obtained by further introducing a crosslinkable functional group (for example, a photopolymerizable functional group) into the above-described naturally occurring polymer and a synthetic polymer, may also be used. By using a modified product having a crosslinkable functional group, the crosslinking density can be controlled, and thereby the compressive modulus of elasticity can be adjusted more easily. In a case in which the synthetic polymer is a graft copolymer, the coefficient of viscosity of the culture substrate surface can be adjusted more easily by adjusting the structure of the graft moiety, the molecular weight, and the like. Regarding the above-mentioned polymer, one kind thereof may be used alone, or two or more kinds thereof may be used in combination.

As an example of the culture substrate, a culture substrate comprising a surface portion having: soft regions that extend side by side along a plurality of directions intersecting each other; and a plurality of stiff regions compartmented by the soft regions and having a higher compressive modulus of elasticity than the soft regions, wherein the stiff regions and the soft regions are disposed such that the cells to be cultured on the surface move isotropically between the stiff regions and the soft regions, may be mentioned.

<Method for Manufacturing Culture Substrate>

An embodiment of the method for manufacturing a culture substrate has: forming a composition layer including a photopolymerizable compound and a photopolymerization initiator, on a support; and irradiating the composition layer with light in a patternwise fashion and thereby obtaining the above-mentioned culture substrate. According to the present manufacturing method, if necessary, the method may have detaching the support.

With regard to the manufacturing method described above, when the composition layer is irradiated with light in a patternwise fashion, regions having different compressive moduli of elasticity are formed on the surface of the culture substrate. At this time, the above-mentioned culture substrate 100 can be produced by controlling the light-irradiated regions such that stiff regions having a high compressive modulus of elasticity are compartmented by soft regions, and the stiff regions have acute angle parts protruding toward the soft regions on the surface of the culture substrate.

In the above-mentioned manufacturing method, first, a composition layer is formed on a support. Regarding the method of forming a composition layer, for example, a method of applying a composition including a photopolymerizable compound and a photopolymerization initiator, and the like may be mentioned. The composition layer may be formed by dissolving the composition in a solvent (for example, water or the like), thereby preparing a solution (for example, an aqueous solution or the like) or a dispersion liquid, and applying this solution or the like on a support, and thereafter, the composition layer may be formed by further removing the solvent as necessary. The thickness of the composition layer may be, for example, 10 to 50 μm.

As the support, for example, a glass substrate, a plastic substrate, and the like can be used. The support may be, for example, a support that has been subjected to surface treatment such as a release treatment and a coating treatment. The coating treatment may be, for example, a treatment of providing a coating formed from a temperature-responsive polymer on the support, or the like. Examples of the temperature-responsive polymer include poly(N-isopropylacrylamide) (pNIPAAm), and the like. By coating the support with a temperature-responsive polymer, it is easy to detach the support from the culture substrate thus formed.

the composition layer is formed from a composition including a photopolymerizable compound and a photopolymerization initiator. A photopolymerizable compound is a compound having a photopolymerizable functional group, and examples include compounds obtained by introducing a photopolymerizable functional group to biologically derived biopolymers such as collagen, gelatin, chitin, chitosan, alginic acid, and hyaluronic acid; acrylic monomers such as acrylamide and ethylene glycol diacrylate; vinylic monomers such as ethylene, propylene, butadiene, isoprene, styrene, and vinyl acetate; silane compounds such as dimethylsiloxane; and the like. Regarding the above-described acrylic monomers, vinylic monomers, and silane compounds, polymers thereof may also be used as the photopolymerizable compounds as long as the polymers have photopolymerizable functional groups. Regarding the above-mentioned photopolymerizable compounds, one kind thereof may be used alone, or two or more kinds thereof may be used in combination.

Examples of the photopolymerizable functional group to be introduced into a biopolymer include ethylenically unsaturated groups such as a vinyl group, an allyl group, a styryl group, and a (meth)acryloyl group; and the like. There may be a plurality of photopolymerizable functional groups to be introduced into a biopolymer, and the photopolymerizable functional group is not limited to one kind but may be a plurality of kinds of functional groups. The introduction ratio of the photopolymerizable functional group may be, for example, 80% to 100% with respect to the total amount of the reactive functional groups present in the biopolymer (for example, in the case of gelatin, an amino group or the like). As the introduction ratio of the photopolymerizable functional group is in the above-described range, the control of the compressive modulus of elasticity of the culture substrate can be made easier.

The photopolymerizable compound preferably includes gelatin into which a photopolymerizable functional group has been introduced (photocurable gelatin). Regarding the photocurable gelatin, for example, a product obtained by introducing a photopolymerizable functional group into the functional groups of the various amino acid residues present in gelatin, or the like may be mentioned. Examples of such a photocurable gelatin include gelatin into which a styryl group has been introduced (also referred to as photocurable styrenated gelatin), and the like.

The photocurable gelatin can be prepared by reacting gelatin with a compound having a photopolymerizable functional group (for example, 4-vinylbenzoic acid or the like) in the presence of a carbodiimide as a condensing agent. For the reaction between gelatin and the compound having a photopolymerizable functional group, a condensing agent may be used. As the condensing agent, for example, a carbodiimide can be used. Examples of the carbodiimide include dicyclohexylcarbodiimide (DCC), diethylcarbodiimide, diisopropylcarbodiimide (DIC), ethylcyclohexylcarbodiimide, diphenylcarbodiimide, 1-ethyl-3-(3-dimethylaminopropyl)carbodiimide hydrochloride (EDC), 1-cyclohexyl-3-(3-dimethylaminopropyl)carbodiimide hydrochloride, and the like. Regarding the above-mentioned condensing agents, one kind thereof may be used alone, or two or more kinds thereof may be used in combination.

In a case in which the photopolymerizable compound is the above-described biopolymer or a polymer, the weight average molecular weight of the photopolymerizable compound may be, for example, 95,000 to 105,000. When the weight average molecular weight of the photopolymerizable compound is in the above-described range, the control of the compressive modulus of elasticity of the culture substrate can be made easier. Incidentally, the weight average molecular weight according to the present specification is a value measured by gel permeation chromatography and is expressed as a value converted relative to polystyrene standards.

Examples of the photopolymerization initiator include carbonyl compounds such as camphorquinone, acetophenone, benzophenone, and dimethoxyphenylacetophenone, and derivatives thereof; sulfur compounds such as dithiocarbamate, xanthogenate, and thiophenol, and derivatives thereof; peroxides such as benzoyl peroxide and butyl peroxide, and derivatives thereof, azobis compounds such as azobisisobutyronitrile and azobisisobutyric acid ester, and derivatives thereof; halogen compounds such as bromopropane and chloromethynaphthalene, and derivatives thereof; azide compounds such as phenyl azide and derivatives thereof; xanthene-based dyes such as rhodamine, erythron, fluorescein, and eosin, and derivatives thereof; riboflavin and derivatives thereof; and the like. Regarding the photopolymerization initiators, one kind thereof may be used alone, or two or more kinds thereof may be used in combination. These photopolymerization initiators preferably include camphor-quinone, and more preferably include sulfonyl camphorquinone, from the viewpoint that the biological safety is excellent. The content of the photopolymerization initiator may be, for example, 0.01% to 10% by mass, or 0.1% to 3% by mass, based on the total mass of the photopolymerizable compound.

The photopolymerizable compound and the photopolymerization initiator may be used after being dissolved in an aqueous solution. Regarding the aqueous solution, an aqueous solution in which stem cells can survive can be used, and examples include physiological salt solutions such as Ringer's solution and Locke's solution; balanced salt solutions such as a phosphate buffer solution, a Tyrode's solution, Hanks' solution, Earle's solution, and Hepes solution; and the like. In the case of using an aqueous solution, the concentration of the photopolymerizable compound may be 20% to 50% by mass, or 25% to 30% by mass, based on the total mass of the aqueous solution.

In the aqueous solution, nutrient components needed for the cultured stem cells to proliferate may be added. Examples of the nutrient components include minerals such as sodium (Na), potassium (K), calcium (Ca), magnesium (Mg), phosphorus (P), and chlorine (Cl), amino acids, vitamins, sugars, fats, growth factors, and the like. These nutrient components can be appropriately selected and used in combination, in accordance with the type of stem cells and the like.

Next, the composition layer is irradiated with light in a patternwise fashion, and thereby the above-mentioned culture substrate is obtained. By irradiating the composition layer with light, for example, the composition layer in the areas irradiated with light is cured, and stiff regions having a high compressive modulus of elasticity are formed. In the composition layer in the areas not irradiated with light, a curing reaction does not proceed, and soft regions having a low compressive modulus of elasticity are formed. Light irradiation of the composition layer is carried out through a negative mask pattern or a positive mask pattern, and thereby it is possible to irradiate the composition layer with light in a patternwise fashion. The shape of the soft regions and the stiff regions on the substrate surface can be adjusted through the selection of the mask pattern.

In the above-described method for producing a culture substrate, light irradiation can be carried out dividedly for several times, depending on the type of the polymer compound or the like. For example, a first light irradiating the entire surface of the composition layer with light, and a second light irradiating the composition layer that has been irradiated with light in the first light irradiating, with light in a patternwise fashion and thereby obtaining the above-mentioned culture substrate, may be carried out. As a first stage, the composition layer is irradiated with uniform light over the entire surface for a short time to establish a basal gel layer. Subsequently, as a second stage, the composition layer is irradiated with light in a patternwise fashion, and thereby the above-mentioned culture substrate is obtained. By subjecting the composition layer to light irradiation of this second stage, the composition layer in the areas that have been subjected to light irradiation of the second stage further undergoes curing as compared to the areas that have not been subjected to light irradiation of the second stage (unirradiated areas), and stiff regions having a high compressive modulus of elasticity are formed. In the composition layer of the areas that have not been subjected to light irradiation of the second stage, additional curing reaction does not proceed, and soft regions having a low compressive modulus of elasticity are formed.

Examples of the light source that is used for the light irradiation include a halogen lamp, a xenon lamp, an incandescent lamp, a mercury lamp, an excimer lamp, an argon ion laser, and the like. The wavelength of the irradiated light may be, for example, 300 to 800 nm. The amount of light exposure of the light irradiation may be, for example, 10 to 300 mW/cm$^2$ or 10 to 100 mW/cm$^2$. The time for light irradiation may be, for example, about 0.5 to 10 minutes. The conditions such as the wavelength of light, the amount of light exposure, and the irradiation time can be appropriately adjusted depending on the types of the photopolymerizable compound and the photopolymerization initiator, the set value of the compressive modulus of elasticity of the stiff regions, and the like.

In a case in which a composition layer is formed as a coating film of a solution (for example, an aqueous solution) or a dispersion liquid, as the solvent around the network structure of the polymer, which is formed concomitantly with the progress of curing of the composition layer, is incorporated and swells the composition layer, a gel is formed. In the photocurable gelatin, the crosslinking density of gelatin increases concomitantly with the progress of curing, and at the same time, the degree of swelling of the gel thus formed is decreased. Thereby, the compressive modulus of elasticity of the stiff regions thus formed is increased.

Another embodiment of the culture substrate is a culture substrate for culturing stem cells and comprises a surface portion having: soft regions that extend side by side along a plurality of directions intersecting each other; and a plurality of stiff regions compartmentalized by the soft regions and having a higher coefficient of viscosity than the soft regions. In the surface portion, the stiff regions have acute angle parts protruding toward the soft regions, and the stem cells can be deformed into a shape that is accommodated within the region of the stiff regions.

The "coefficient of viscosity" according to the present specification means the viscosity coefficient that is generally defined for a viscoelastic body, and is a value obtained by dividing the shear stress obtainable in a case in which a shear flow is applied in a horizontal direction to the viscoelastic body using an arbitrary flat plate, by the shear rate gradient. The "coefficient of viscosity" according to the present specification can be measured by a horizontal frictional force measuring method of using an atomic force microscope (AFM) for a substance layer that constitutes the surface portion provided on the culture substrate. A cantilever of the AFM is scanned horizontally with respect to the substance layer, and the frictional force as shear stress exhibited by the substance layer from the torsion in the horizontal direction of the cantilever is measured. Thereafter, the scanning rate of the cantilever, that is, the shear rate, is set as a set value, and the coefficient of viscosity can be calculated from the shear stress thus obtainable and the shear rate gradient.

The stiff regions may have a higher coefficient of viscosity than the soft regions. As the surface of the culture substrate comprises a plurality of regions having different coefficients of viscosity, when the cultured cells move over the plurality of above-described regions, it is possible to change the stimulation that the cells receive from the substrate surface. That is, the mechanical stimulation sensed by the cells cultured on the culture substrate can be varied at a high frequency over the culture period. The coefficient of viscosity of the stiff regions may be 10 or more times, 100 or more times, or 1,000 or more times, the coefficient of viscosity of the soft regions. The coefficient of viscosity of the soft regions may be 10,000 or less times, or 5,000 or less times, the coefficient of viscosity of the stiff regions. By adjusting the coefficient of viscosity of the stiff regions to the above-described range, the difference between the stimulation from the stiff regions and the stimulation from the soft regions can be made more easily recognizable by stem cells. When the stimulation that stem cells receive is varied at a high frequency over the culture period, the undifferentiated state of the stem cells can be more sufficiently maintained.

The coefficient of viscosity of the stiff regions can be adjusted by means of the type of the stem cells as a culturing target, the stage of differentiation, and the like.

The coefficients of viscosity of the stiff regions and the soft regions can be determined, for example, as follows. For example, explanation will be given by assuming the culture of human mesenchymal stem cells (hMSC). In the case of hMSC, the respective appropriate coefficients of viscosity of the stiff regions and the soft regions may be determined by utilizing the fact that the migration of YAP to the cell nucleus is affected by the stimulation that hMSC receives from the substrate. That is, the respective appropriate coefficients of viscosity of the stiff regions and the soft regions in the culture substrate for culturing hMSC can be determined by observing the intracellular behavior of transcriptional coactivator YAP, which is known to be involved in the determination of the differentiation lineage of hMSC. First, a plurality of culture substrates having different coefficients of viscosity is prepared, culture of hMSC is carried out on each of the culture substrates, and the sites where YAP is localized within cells are specified. By performing such an observation, the threshold value of the coefficient of viscosity of elasticity of the substrate in relation to whether YAP will migrate to the cell nucleus or remain in the cytoplasm, is determined. Then, the coefficient of viscosity of the stiff regions and the coefficient of viscosity of the soft regions can be determined so as to exceed the determined threshold value. In the above-described example, the coefficients of viscosity of the stiff regions and the soft regions are determined on the basis of the intracellular behavior of YAP; however, attention may also be paid to other factors, depending on the target stem cells or the like. As the other factors, proteins known to be such that migration thereof to the cell nucleus is affected in accordance with the stimulation from the substrate can be employed, and examples include TAZ, RUNX2, and the like.

<Method for Manufacturing Culture Substrate>

An embodiment of the method for manufacturing a culture substrate has: surface-immobilizing a photoreactive radical polymerization initiator to a support; and providing a layer containing a compound having a photopolymerizable functional group on the support and irradiating the layer with light in a patternwise fashion. The layer may be, for example, a layer including a solution containing a compound having a vinyl group. The irradiating with light may be, for example, graft polymerizing the above-described compound having a photopolymerizable functional group in a light-irradiated part by light irradiation through a photomask, using the above-described photoreactive radical polymerization initiator as a starting point, and obtaining a graft-polymerized layer. Through the irradiating with light, for example, portions where a graft polymer has been formed (photopolymerized layer-forming part) and portions of the support surface (non-photopolymerized layer-forming part) can be formed on the support surface, and stiff regions and soft regions can be formed. Light irradiation may be carried out dividedly for several times. In such a case, first, a graft polymer is uniformly formed on the support surface by light irradiation of a first time, subsequently light irradiation of a second time is performed as light irradiation through a photomask, and thereby portions having different lengths of the graft chains can be formed. That is, by using light irradiation for several times, a graft-polymerized layer having a plurality of regions having different thicknesses of the graft layer can be formed.

With regard to the manufacturing method described above, in order to achieve patterning of stiff regions and soft regions non-uniformly, a surface photograft polymerization method imitating the method of photolithography can be used. For example, patterning of the graft-polymerized layer is enabled by using a photo-iniferter (for example, above-mentioned Non Patent Literatures 3 and 4, and the like). In surface graft polymerization using a photo-iniferter, the molecular chain shape of the graft polymer grows almost linearly depending on the time of light irradiation and the light intensity at the time of light irradiation. For this reason, compartments having different thicknesses of the graft-polymerized layer can be patterned by adjusting the light irradiation time and the light intensity at the time of performing light irradiation using a photomask. Incidentally, in a surface-initiated atom transfer radical polymerization method that is frequently used for surface graft polymerization, the non-uniform patterning surface modification having stiff regions and soft regions according to the present disclosure cannot be carried out.

Examples of the polymerization initiator capable of surface immobilization, which can be used for photo-iniferter polymerization, include N,N-diethyl dithiocarbamate trihydrochloride, N-dithiocarboxysarcosine, and the like. Examples of the compound having a photopolymerizable functional group include a vinyl monomer and the like. Examples of the vinyl monomer include N-isopropylacrylamide, dimethylacrylamide, and the like. In order to provide a layer containing a compound having a photopolymerizable functional group, a solution obtained by dissolving the above-mentioned compound having a photopolymerizable functional group in an appropriate solvent can be used.

By regulating the thickness of the graft-polymerized layer, the coefficient of viscosity of the surface portion can be adjusted. The coefficient of viscosity of the surface significantly affects the adhesion and spreading area of stem cells and can be involved in the differentiation lineage bias. Thus, by regulating the light irradiation time and the light intensity and regulating the thickness of the graft-polymerized layer, the coefficients of viscosity of the stiff regions and the soft regions can be prepared to appropriate values.

<Culturing Device>

An embodiment of the culturing device is a culturing device having stem cells and a culture substrate for culturing the stem cells, and the culture substrate comprises a surface portion having: soft regions that extend side by side along a plurality of directions intersecting each other; and a plurality of stiff regions compartmented by the soft regions and having a higher compressive modulus of elasticity than the soft regions. In the surface portion, the stiff regions have acute angle parts protruding toward the soft regions, and the stem cells can be deformed into a shape that is accommodated within the region of the stiff regions.

Another embodiment of the culturing device is a culturing device having stem cells and a culture substrate for culturing the stem cells, and the culture substrate comprises a surface portion having: soft regions that extend side by side along a plurality of directions intersecting each other; and a plurality of stiff regions compartmented by the soft regions and having a higher coefficient of viscosity than the soft regions. In the surface portion, the stiff regions have acute angle parts protruding toward to the soft regions, and the stem cells can be deformed into a shape that is accommodated within the region of the stiff regions.

<Culturing Method>

An embodiment of the method for culturing stem cells includes culturing stem cells on the above-mentioned culture substrate. The method for culturing stem cells may be an embodiment including culturing the stem cells in a state in which the above-mentioned culture substrate and stem cells are in contact with each other. By using the above-mentioned culture substrate as a culture substrate for stem cells, stem cells can be proliferated while differentiation of the stem cells is suppressed. In other words, it can be said that the method for culturing stem cells according to the present embodiment provides a method for producing a large quantity of undifferentiated cells.

The method for culturing stem cells can culture stem cells while sufficiently maintaining an undifferentiated state, even without using an unknown and undefined differentiation inhibitory factor that is prepared and supplied from animal blood serum or the like, by using the above-mentioned culture substrate. In the case of mesenchymal stem cells, a differentiation inhibitory factor that effectively suppresses differentiation and a differentiation and proliferation factor related to the maintenance of undifferentiability and pluripotency have not been established. Conventionally, with regard to the culture of stem cells using a conventional cell culture dish and a standard medium, it has been implemented to select and add a factor that is considered to be effective for the sustenation of stem cells at every time of culturing. With regard to the method for culturing stem cells, it is not necessary to select and use components derived from animal blood serum and the like, and it is also possible to avoid the stimulation from the substrate being accumulated in the stem cells during culture. Therefore, the quality, safety, and the like of proliferated stem cells thus obtained can be further enhanced. Since the stem cells cultured by the method for culturing stem cells according to the present embodiment can be of stable quality while maintaining an undifferentiated state, the stem cells can be useful as stem cells for research and regenerative medicine.

The method for culturing stem cells as described above uses the above-mentioned culture substrate, and thus the contents of explanation regarding the above-mentioned culture substrate and the method for manufacturing a culture substrate can be applied. In contrast, the explanation of the method for culturing stem cells according to the present embodiment can be applied to the above-mentioned culture substrate and the method for manufacturing a culture substrate.

Stem cells are cells that have not been differentiated, and mean cells having pluripotency and self-renewal capability. Examples of the stem cells include induced pluripotent stem cells (iPS cells), embryonic stem cells (ES cells), and the like. iPS cells and ES cells are pluripotent stem cells having a capability of differentiating into three germ layers of ectoderm, mesoderm, and endoderm, and all types of cells produced by differentiation of the three germ layers. The above-described method for culturing stem cells can also be used for culturing somatic stem cells in which pluripotent stem cells have been differentiated into several stages.

Examples of the somatic stem cells include hematopoietic stem cells, neural stem cells, hepatic stem cells, vascular endothelial stem cells, mesenchymal stem cells (MSC), and the like. Examples of the mesenchymal stem cells include stem cells that are differentiated into mesoderm-derived stromal cells (bone marrow), osteoblasts (osteocytes), chondroblasts (chondrocytes), adipocytes, muscle cells, fibroblasts (tendons, ligaments), vascular endothelial cells, and the like.

Regarding the culturing conditions for stem cells, conditions can be selected according to the type of cells to be cultured, and the culturing conditions used for subculture that is carried out on a medium such as conventional Matrigel (BD Matrigel™ Basement Membrane Matrix: BD 354234) can be applied.

With regard to the culture of stem cells using the culture substrate of the present disclosure, differentiation of the stem cells during culture is suppressed. For example, with regard to the culture of stem cells using the culture substrate of the present disclosure, in a case in which culture is carried out in a culture fluid including a growth factor that induces bone differentiation of stem cells or the like (for example, manufactured by R&D Systems, Inc., trade name: Osteogenic Supplement, or the like), resistance to differentiation is observed, and in a case in which the culture system is returned to a conventional culture substrate and similar differentiation is induced, normal bone differentiation ability is exhibited. That is, during culture using the culture substrate of the present disclosure, the stem cells do not express responsiveness to differentiation stimulation, maintain normal differentiation ability while in a state of avoiding a bias in differentiation, and can maintain high undifferentiability. Therefore, the method for culturing stem cells using the culture substrate of the present disclosure, and the culturing device are useful for the culture of stem cells in an undifferentiated state.

The stem cells cultured using the culture substrate of the present disclosure can exhibit a superior differentiation ability than stem cells cultured using a conventional culture substrate. The inventors of the present invention speculate that in the culture using the culture substrate of the present disclosure, the stem cell characteristics intrinsically possessed by the stem cells as an object of culture are restored. For example, when a stem cell population whose bone differentiation induction efficiency is originally not very high is cultured using the culture substrate of the present disclosure, the amount of calcium production that exhibits terminal differentiation efficiency can be increased. Therefore, the method for culturing stem cells using the culture substrate of the present disclosure, and the culturing device are suitable for the culture of stem cells. Furthermore, the method for culturing stem cells using the culture substrate of the present disclosure, and the culturing device are considered useful also for the preparation of a stem cell group that serves as a standard for checking the quality of stem cells.

Stem cells cultured using the culture substrate of the present disclosure can have superior proliferation properties than stem cells cultured using a conventional culture substrate. For example, in the case of preparing stem cells that are used after being transplanted into a living body, a predetermined quantity of stem cells can be prepared more rapidly, and the time period for initiating administration to a patient can be shortened. Therefore, the method for culturing stem cells using the culture substrate of the present disclosure, and the culturing device are useful.

Stem cells cultured using the culture substrate of the present disclosure can have superior motility than stem cells cultured using a conventional culture substrate. For example, in a case in which stem cells are used after being transplanted in a living body, it is considered that since the stem cells have excellent motility as described above, the cells can easily reach a desired site (for example, a diseased site or the like). Therefore, the method for culturing stem cells using the culture substrate of the present disclosure, and the culturing device are useful.

In stem cells cultured using the culture substrate of the present disclosure, the expression intensity of a gene in a band boundary region of the chromosome can be increased. The expression intensity of a gene can be checked from the results of a comprehensive gene analysis on the above-described stem cells and a chromosome map that can be acquired from a gene database (for example, UNIVERSITY of CALIFORNIA, SANTA CRUZ, Genomics Institute, or the like). Although the reason why effects such as described above are obtained is not clearly known, the inventors of the present invention speculate that it is because since the variations at a high frequency of the mechanical stimulation that stem cells receive from the culture substrate surface propagate also to the nucleus of the stem cells, these variations of the mechanical stimulation cause stress concentration at the boundaries of the chromosome bands. It is thought that since the boundary positions of the chromosome bands are also portions before and after which the rigidity of the chromosome is switched, stress concentration such as described above can occur. In the chromosome band regions where stress concentration occurs, due to an increase in the fluctuation of the higher-order structure, the gene group located there can enhance the interaction between various transcription factors and transcription regulatory factors. Therefore, the method for culturing stem cells using the culture substrate of the present disclosure, and the culturing device can also be applied as a method for increasing the expression intensity of genes near the boundaries of the chromosome bands.

Thus, several embodiments of the present disclosure have been described; however, the present disclosure is not intended to be limited to the above-described embodiments. Furthermore, the contents of explanation concerning the above-mentioned embodiments can be mutually applied.

EXAMPLES

Hereinafter, the contents of the present disclosure will be described in more detail with reference to Examples and Comparative Examples. However, the present disclosure is not intended to be limited to the following Examples.

Example 1

<Production of Culture Substrate>

Solution A was prepared by mixing an aqueous solution of styrenated gelatin (StG) with an aqueous solution of Sulfonyl Camphorquinone (SCQ) as a photopolymerization initiator (final StG concentration: 30% by mass, final SCQ concentration: 1.5% by mass). Next, two sheets of round glass plates having a diameter of 1.8 cm [two sheets of a round glass plate (diameter: 1.8 cm) comprising a surface coating formed of poly(N-isopropylacrylamide) (pNIPAAm) as a sacrificial layer and a vinyl group-modified round glass plate (diameter: 1.8 cm)] were prepared, and 20 µL of solution A was interposed between the two sheets of round glass plates. A base gel (basal gel layer) having a low compressive modulus of elasticity was produced by irradiating the solution A (first light irradiation) with about 60 mW/cm$^2$ of continuous light for 300 seconds.

Figure 2:
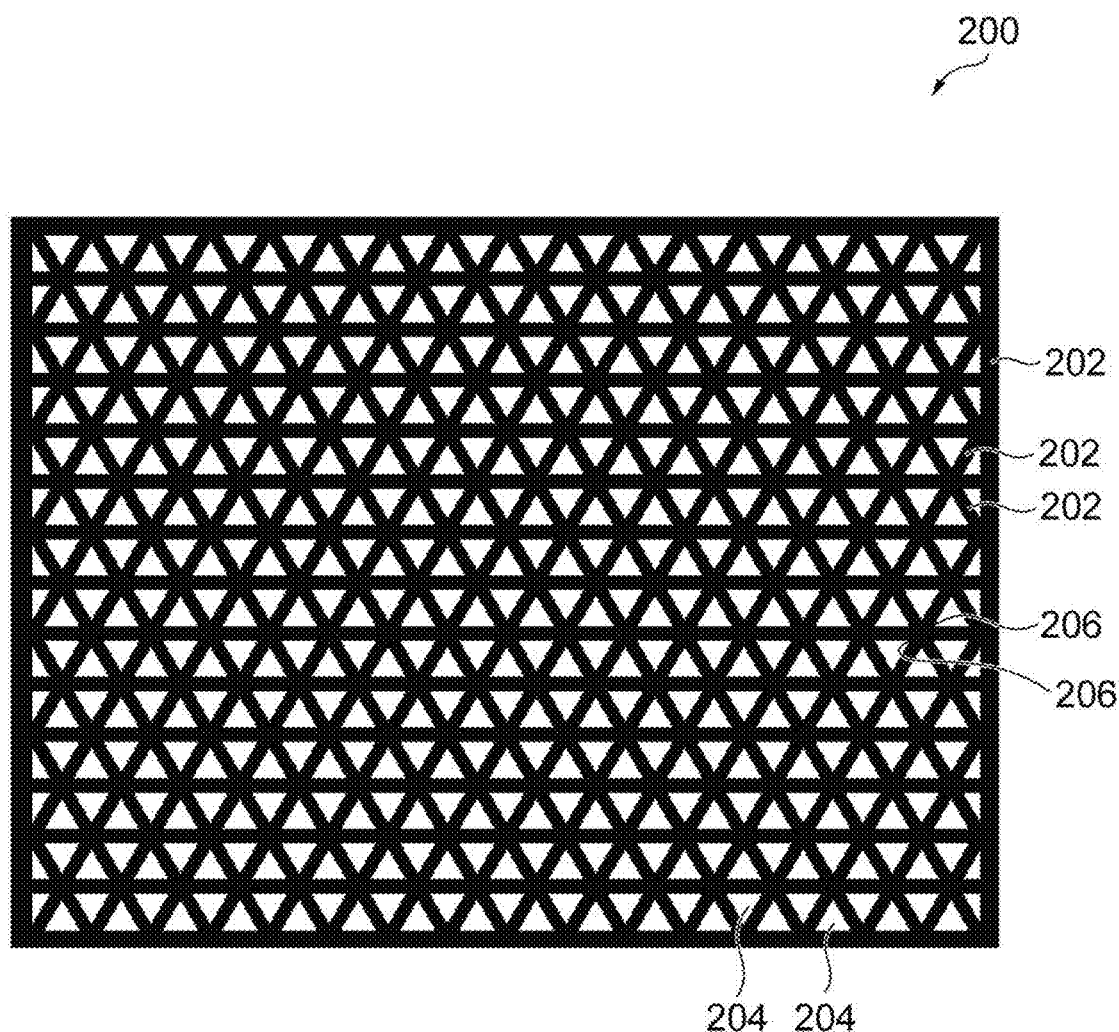
FIG. 2 is a schematic diagram of a photomask used in Example 1.

Next, the base gel obtained as described above was irradiated (second light irradiation) with about 200 mW/cm$^2$ of light in a patternwise fashion through a photomask for 90 seconds, subsequently the base gel was washed by shaking in a phosphate buffer saline (PBS) overnight, and thereby a patterned culture substrate (patterned gel substrate) was prepared. Here, regarding the photomask, a photomask 200 shown in FIG. 2 was used. The photomask 200 has a light blocking part 202 and a plurality of triangular-shaped openings 204 formed such that one side measured 150 µm. In the photomask 200, the distance between apexes 206 of each triangular-shaped opening 204 was 120 µm. For the patterned gel substrate thus obtained, the compressive modulus of elasticity was measured using an atomic force microscope (AFM, manufactured by JPK Instruments AG). The measurement of the compressive modulus of elasticity was carried out by performing measurement at 16×16 points in a region having a size of 100 µm×100 µm, and calculating the average value thereof. For the patterned gel substrate, the compressive modulus of elasticity of the stiff regions was 30 kPa, and the compressive modulus of elasticity of the soft regions was 2 kPa.

<Evaluation of Culturing Performance>

Figure 3:
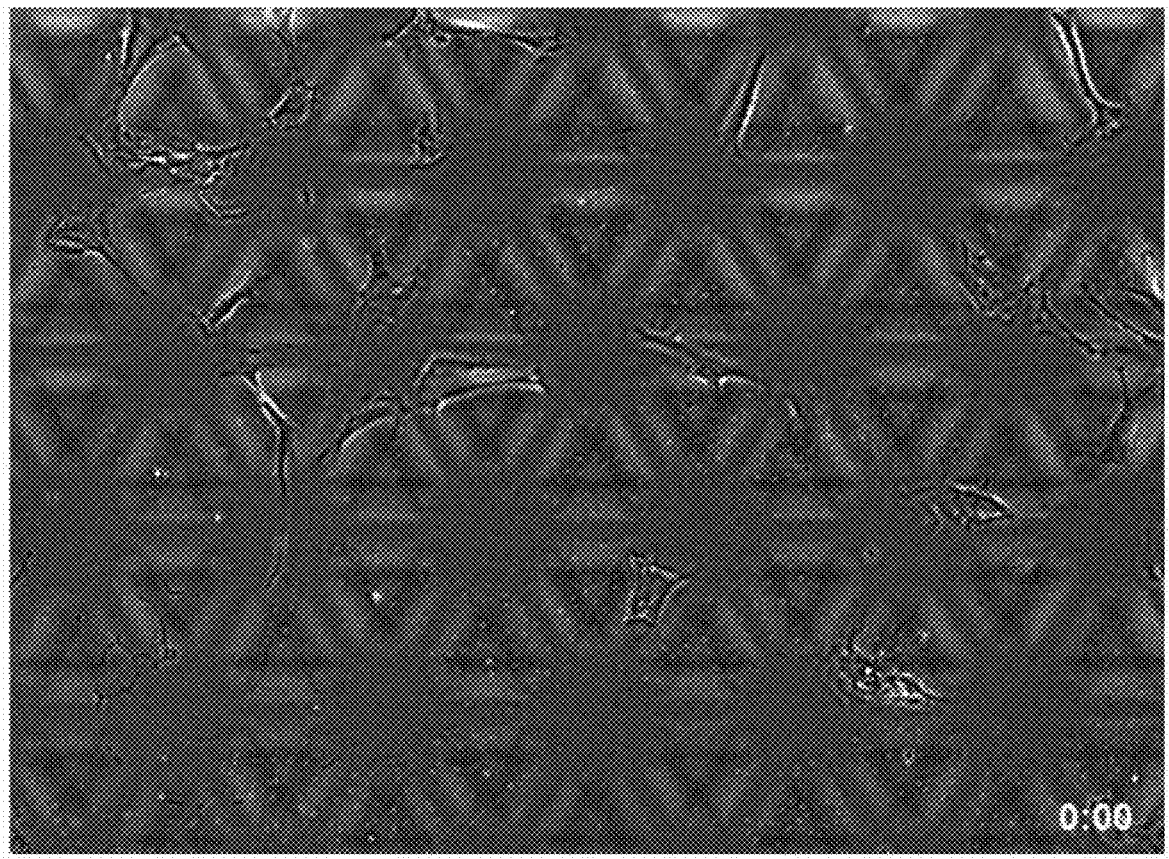
FIG. 3 is a diagram illustrating a portion of the circumstances of evaluation of the culturing performance in Example 1.
Figure 5:
FIG. 5 is a graph showing the time taken by stem cells to stay on stiff regions and soft regions during culture.
Figure 6:
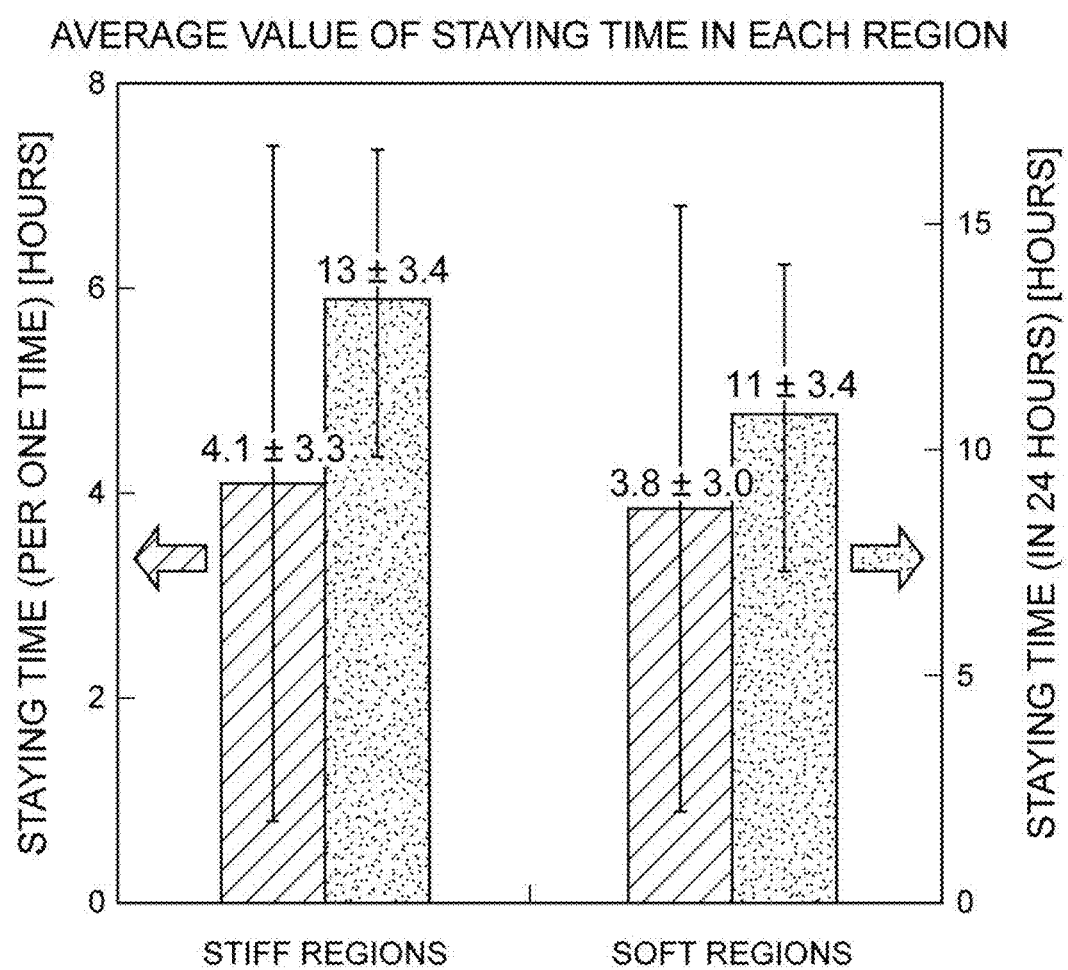
FIG. 6 is a graph showing the average time taken by stem cells to stay on stiff regions and soft regions during culture.

Culture was performed on the patterned gel substrate obtained as described above using human mesenchymal stem cells (hMSC), and thereby an evaluation of the culturing performance was carried out. Incidentally, the size of the human mesenchymal stem cells was 1,000 to 13,000 µm$^2$. A portion of the circumstances of evaluation of the culturing performance in Example 1 is shown in FIG. 3. The patterned gel substrate obtained as described above was subjected to a sterilization treatment and washing using ethanol. On the patterned gel substrate after washing, hMSC was seeded at a concentration of 1,500 cells/cm$^2$, Dulbecco Modified Eagle Medium (DMEM medium, including 10% of fetal bovine serum (FBS)) was added thereto, and then in order to accelerate adhesion of the cells to the substrate, the cells were incubated overnight in an incubator in which the environment had been adjusted to 5% $CO_2$. Thereafter, a time-lapse observation was carried out every 15 minutes using a fluorescence microscope (manufactured by KEYENCE CORPORATION, BZ-X-700). From the time-lapse data thus obtained, twenty cells were randomly extracted, and the locus of movement for 24 hours was analyzed using Image J software. The results are shown in FIG. 4 to FIG. 6.

Figure 4:
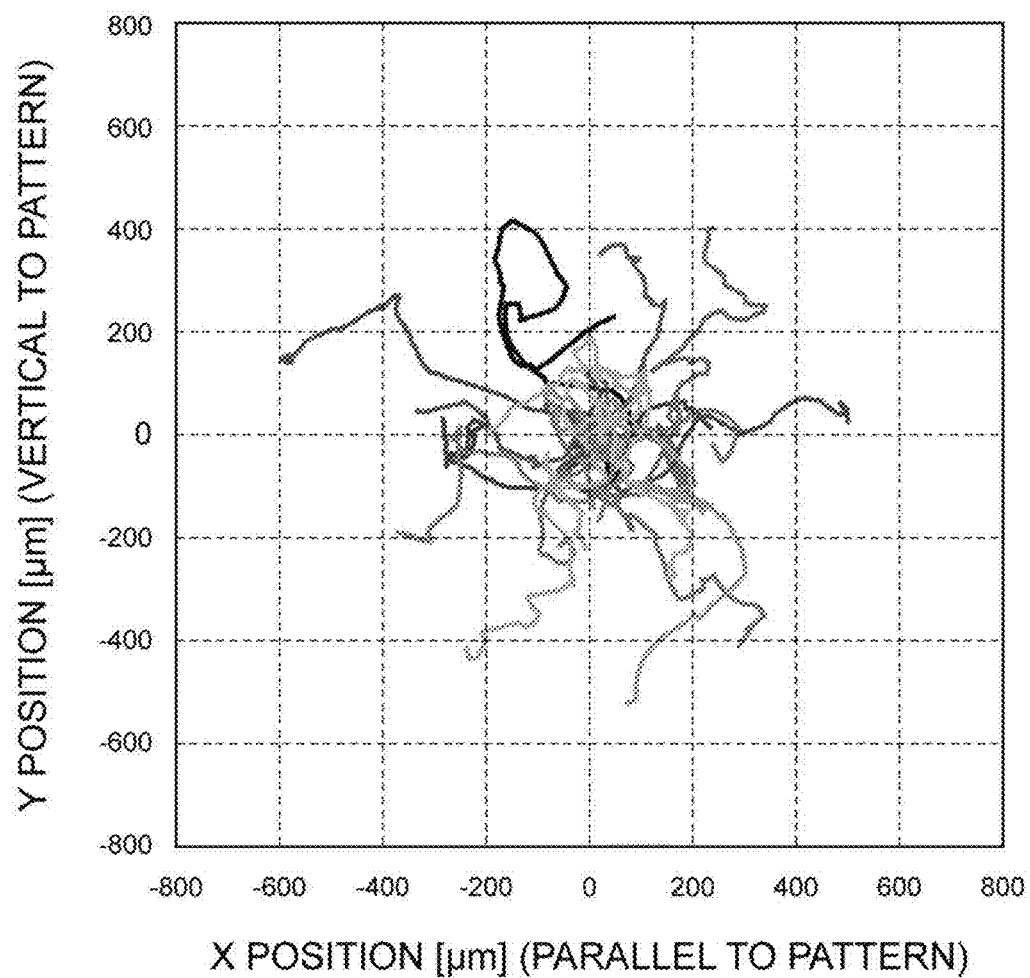
FIG. 4 is a graph showing the inclination of movement of stem cells during culture.

FIG. 4 is a graph showing the tendency of movement of stem cells during culture and is a summary of the movement loci of twenty cells, with the starting point of the movement locus of each of the twenty cells as the origin. FIG. 5 is a graph showing the time in which the stem cells stayed on the stiff regions and the soft regions during culture. FIG. 6 is a graph showing the average times in which the stem cells stayed on the stiff regions and the soft regions during culture. From the results shown in FIG. 4, it was confirmed that the stem cells were moving on the substrate surface without being biased in one direction. Furthermore, from the results shown in FIG. 5 and FIG. 6, it was confirmed that the stem cells stayed on the stiff regions and on the soft regions for substantially the same time, and in combination with the results shown in FIG. 4, the stimulation that stem cells receive can be varied at a high frequency over the culturing period.

Comparative Example 1

<Production of Culture Substrate>

Figure 7:
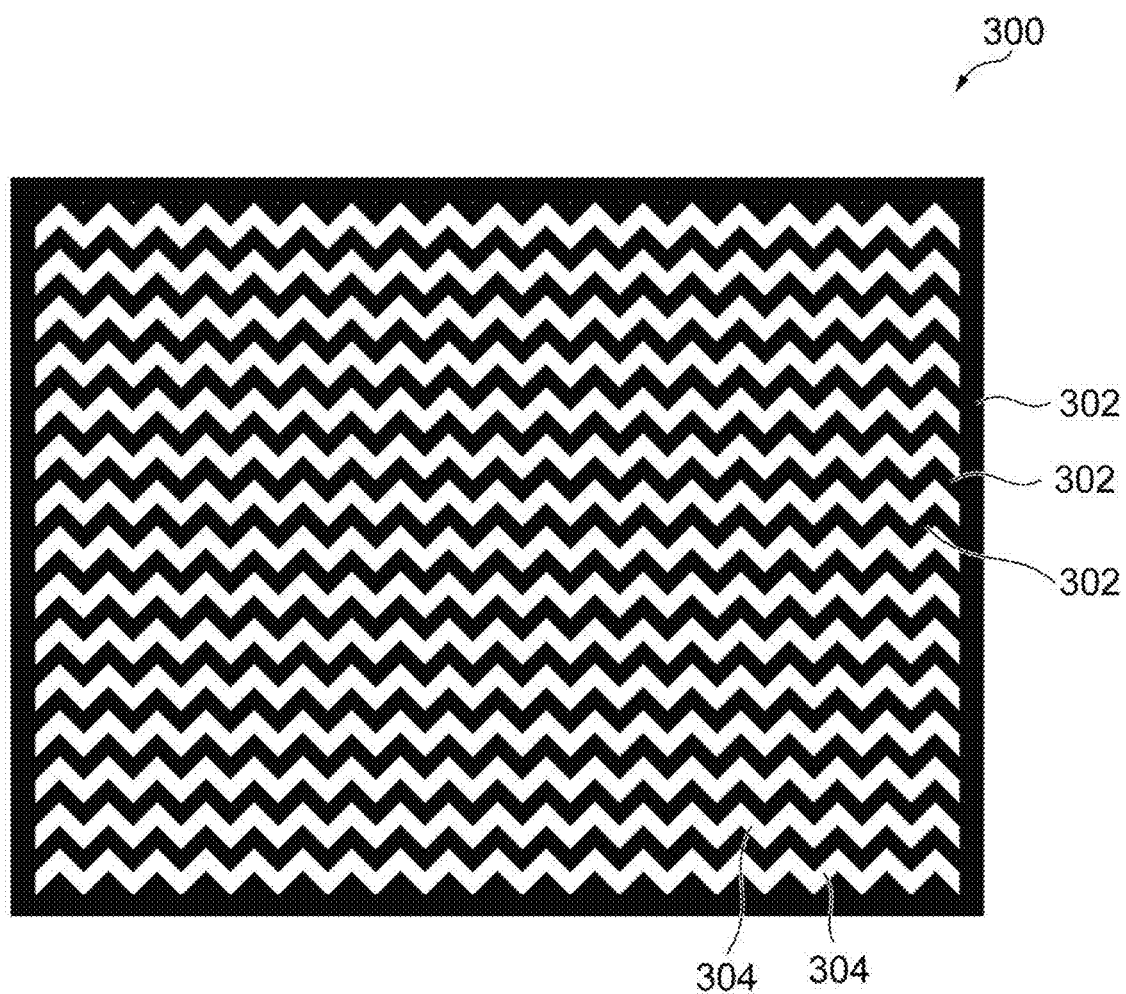
FIG. 7 is a schematic diagram of a photomask used in Comparative Example 1.
Figure 9:
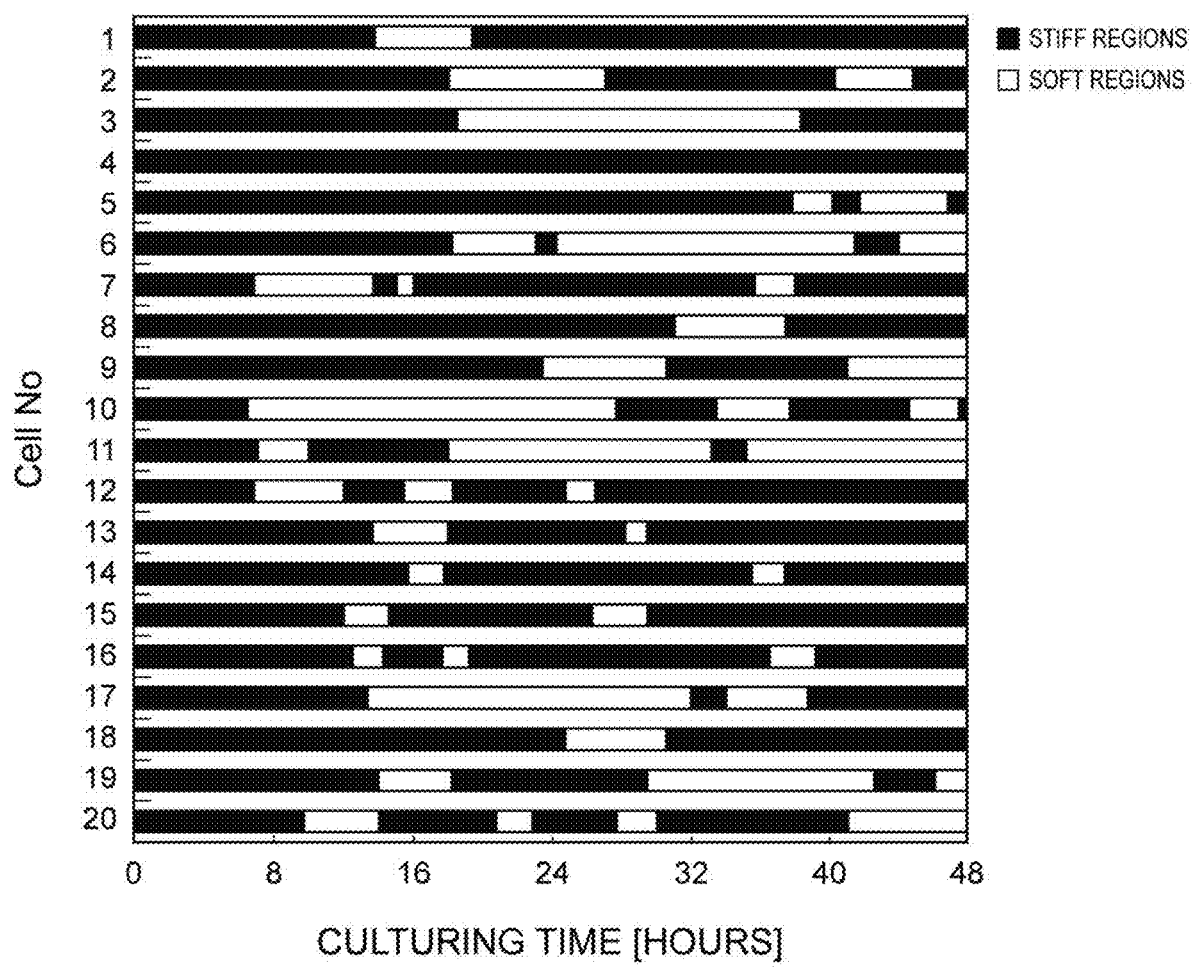
FIG. 9 is a graph showing the time taken by stem cells to stay on stiff regions and soft regions during culture.
Figure 10:
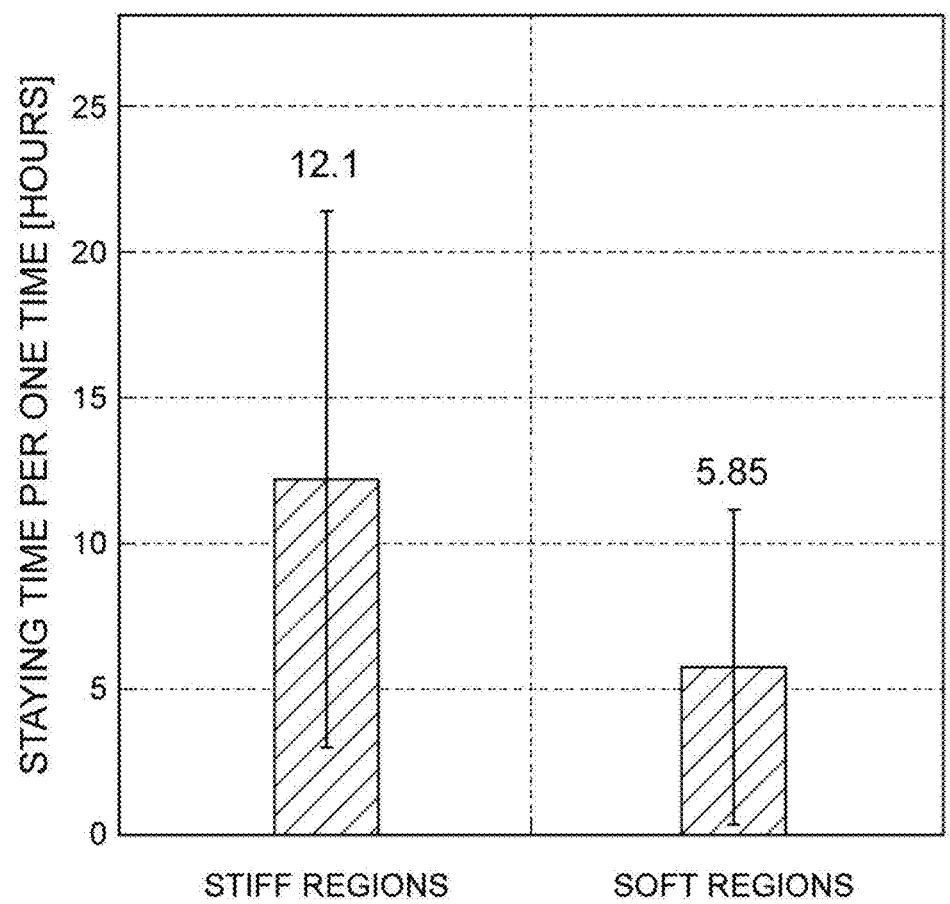
FIG. 10 is a graph showing the average time taken by stem cells to stay on stiff regions and soft regions during culture.

A culture substrate was prepared in the same manner as in Example 1, except that the photomask 300 shown in FIG. 7 was used instead of the mask pattern used in Example 1, and an evaluation of the culturing performance was carried out. Incidentally, with regard to the culture substrate thus obtained, the compressive modulus of elasticity of the stiff regions was 30 kPa, and the compressive modulus of elasticity of the soft regions was 2 kPa. The photomask 300 shown in FIG. 7 has a light blocking part 302 and a plurality of zigzag-shaped openings 304. The zigzag-shaped openings 304 are such that the length of one side is 150 µm, and a pattern of making a turn at an angle of 90° at every 150 µm is formed. Furthermore, the line width was set to 100 μm. The evaluation results are shown in FIG. 8 to FIG. 10.

Figure 8:
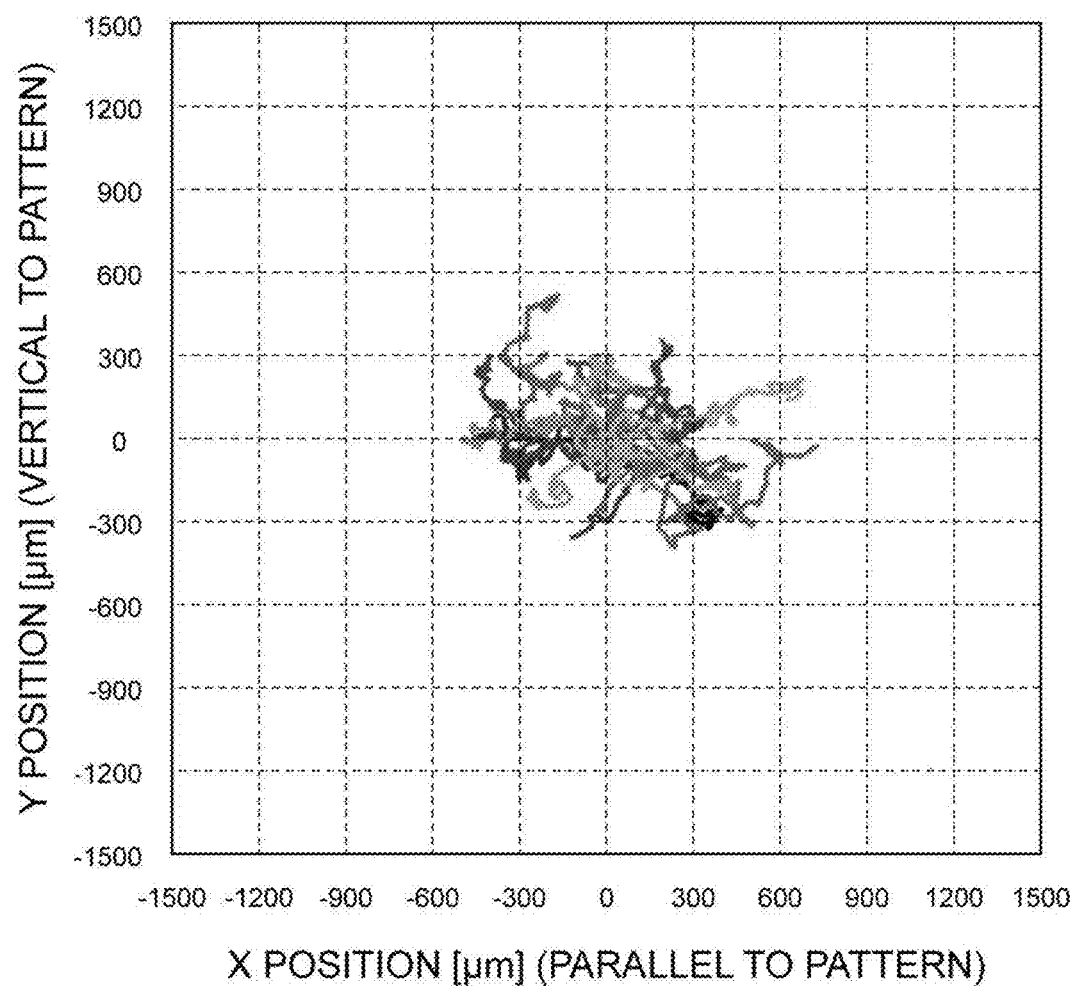
FIG. 8 is a graph showing the inclination of movement of stem cells during culture.

FIG. 8 is a graph showing the tendency of movement of stem cells during culture. FIG. 9 is a graph in which the times taken by stem cells to stay on the stiff regions and the soft regions during culture are described. FIG. 10 is a graph showing the average times taken by stem cells to stay on the stiff regions and the soft regions during culture. From the results shown in FIG. 8, it was verified that the movement locus of the stem cells was biased in the direction of extension of stiff regions or soft regions on the culture substrate. Furthermore, from the results shown in FIGS. 9 and 10, it was verified that the stem cells stayed a longer time on the stiff regions. From these results, it was verified that during culture, stem cells have a possibility that the differentiation determination process may be affected by accumulation of the stimulation that the stem cells receive from the stiff regions.

Comparative Example 2

A culture substrate was prepared in the same manner as in Example 1, except that a base gel having a low compressive modulus of elasticity was irradiated with light over the entire surface without using a photomask. The culture substrate thus obtained did not have a pattern, and the compressive modulus of elasticity of the culture substrate was 30 kPa.

Comparative Example 3

The base gel (basal gel layer) having a low compressive modulus of elasticity that was obtained in the middle of the production of the culture substrate shown in Example 1 was prepared, and this was used as the culture substrate of Comparative Example 3. The culture substrate thus obtained did not have a pattern, and the compressive modulus of elasticity of the culture substrate was 2 kPa.

Reference Example

For reference, a commercially available plastic Petri dish for cell culture (Tissue Culture Polystyrene Dish manufactured by TPP Techno Plastic Products AG) was prepared.

<Evaluation of Culturing Performance: Observation of Intracellular Behavior of YAP>

The intracellular behavior of transcriptional coactivator YAP in stem cell culture was evaluated using the culture substrates obtained in Example 1, Comparative Example 2, and Comparative Example 3. The evaluation of the intracellular behavior of YAP was carried out by first subjecting YAP to fluorescent immunostaining and then making an observation with a fluorescent microscope. The results are shown in FIG. 11 and FIG. 12.

FIG. 11 is a diagram showing fluorescent microscopic photographs showing the localization of YAP inside the stem cells on the culture substrates. FIG. 12 is a graph showing the results of evaluating the localization of YAP inside the stem cells on the culture substrates. In the graph shown in FIG. 12, the position of localization of YAP was observed from the fluorescent microscopic images shown in FIG. 11, the stem cells were classified into a group in which YAP existed mainly in the nucleus (in FIG. 12, indicated as "Nuclear"), a group in which YAP existed mainly in the cytoplasm outside the nucleus (in FIG. 12, indicated as "Cytoplasma"), and a group in which YAP was spread in the cell and was not localized (in FIG. 12, indicated as "Nuclear+Cytoplasma"), and the proportions are shown.

Figure 12:
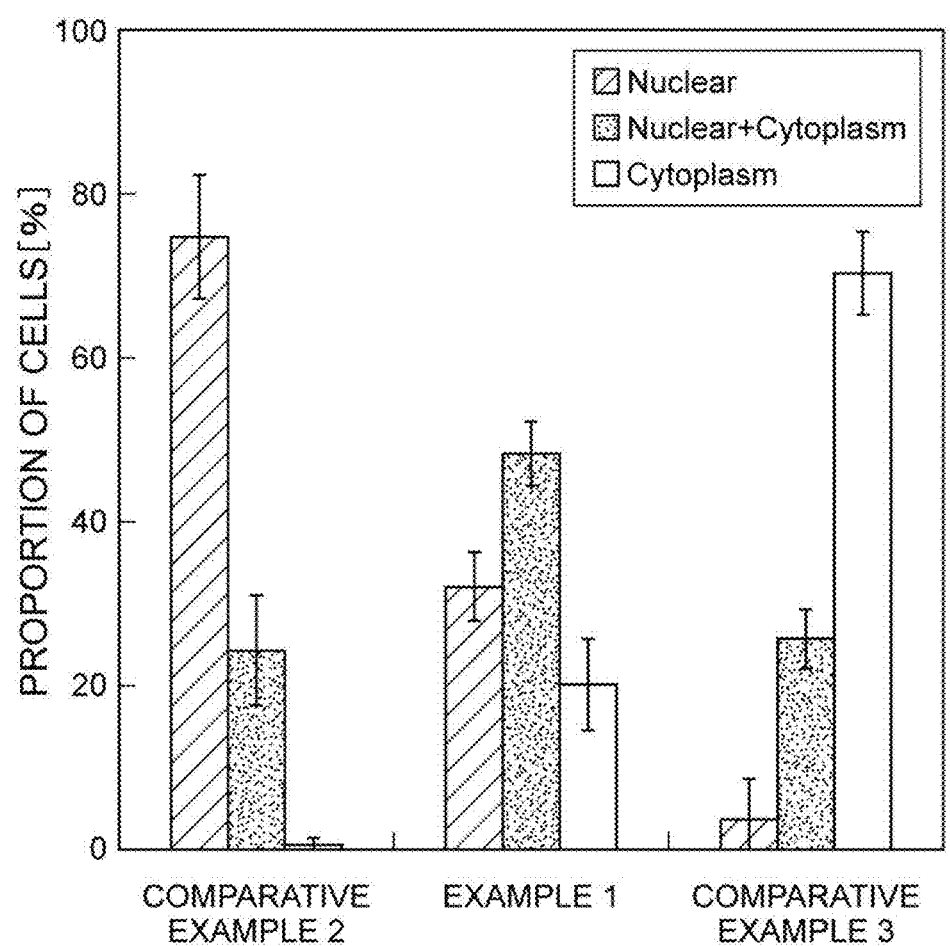
FIG. 12 is a graph showing the results of evaluating the localization of YAP inside stem cells on a culture substrate.

From the results shown in FIG. 11 and FIG. 12, it was verified that in a case in which the culture substrate of Comparative Example 2 (stiff substrate) was used, the stem cells belonging to the group in which YAP had migrated into the nucleus occupied 70% or more of the entirety, and in a case in which the culture substrate of Comparative Example 3 (soft substrate) was used, the stem cells belonging to the group in which YAP was localized in the cytoplasm occupied 70% or more of the entirety. Furthermore, in a case in which the patterned gel substrate of Example 1 was used, stem cells respectively belonging to the group in which YAP was localized in the nucleus, the group in which YAP was localized in the cytoplasm, and the group in which localization of YAP was not seen, were observed, and it was verified that the amounts of existence of the cells were also close to one another. It is speculated that since the stem cells cultured on the patterned gel substrate of Example 1 moved between stiff regions and soft regions, the stimulation received from the substrate varied at a high frequency, and concomitantly with this, the stem cells migrated between the three groups described above. From these results, it was verified that by using a culture substrate such as Example 1, the differentiation biasing stimulation to the stem cells was avoided.

<Evaluation of differentiation ability of stem cells during culture and after culture>

Figure 15:
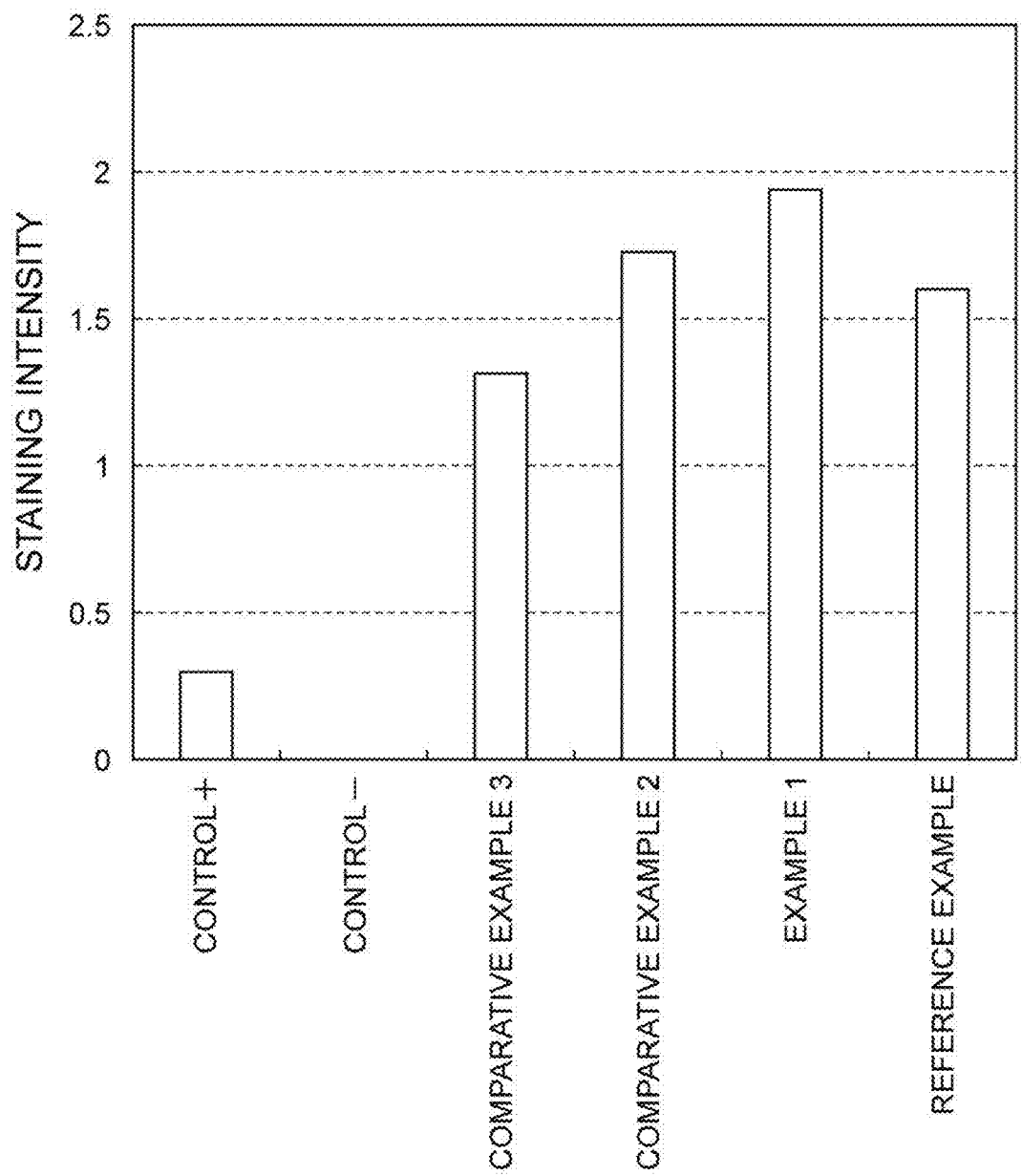
FIG. 15 is a graph showing the results of subjecting stem cells that have been collected after culture to the induction of differentiation.

Culture of human mesenchymal stem cells (hMSC) was carried out using the culture substrates obtained in Example 1, Comparative Example 2, and Comparative Example 3 and the plastic Petri dish for cell culture of Reference Example, and the bone differentiation inducing behavior for hMSC during culture and after culture was evaluated. The bone differentiation induction of hMSC was carried out by culturing hMSC from two weeks to three weeks in a culture fluid including a growth factor that induces bone differentiation of stem cells or the like (for example, manufactured by R&D Systems, Inc., trade name: Osteogenic Supplement). The results are shown in FIG. 13, FIG. 14, and FIG. 15.

<Evaluation of Differentiation Ability of Stem Cells During Culture Using Various Culture Substrates>

Figure 13:
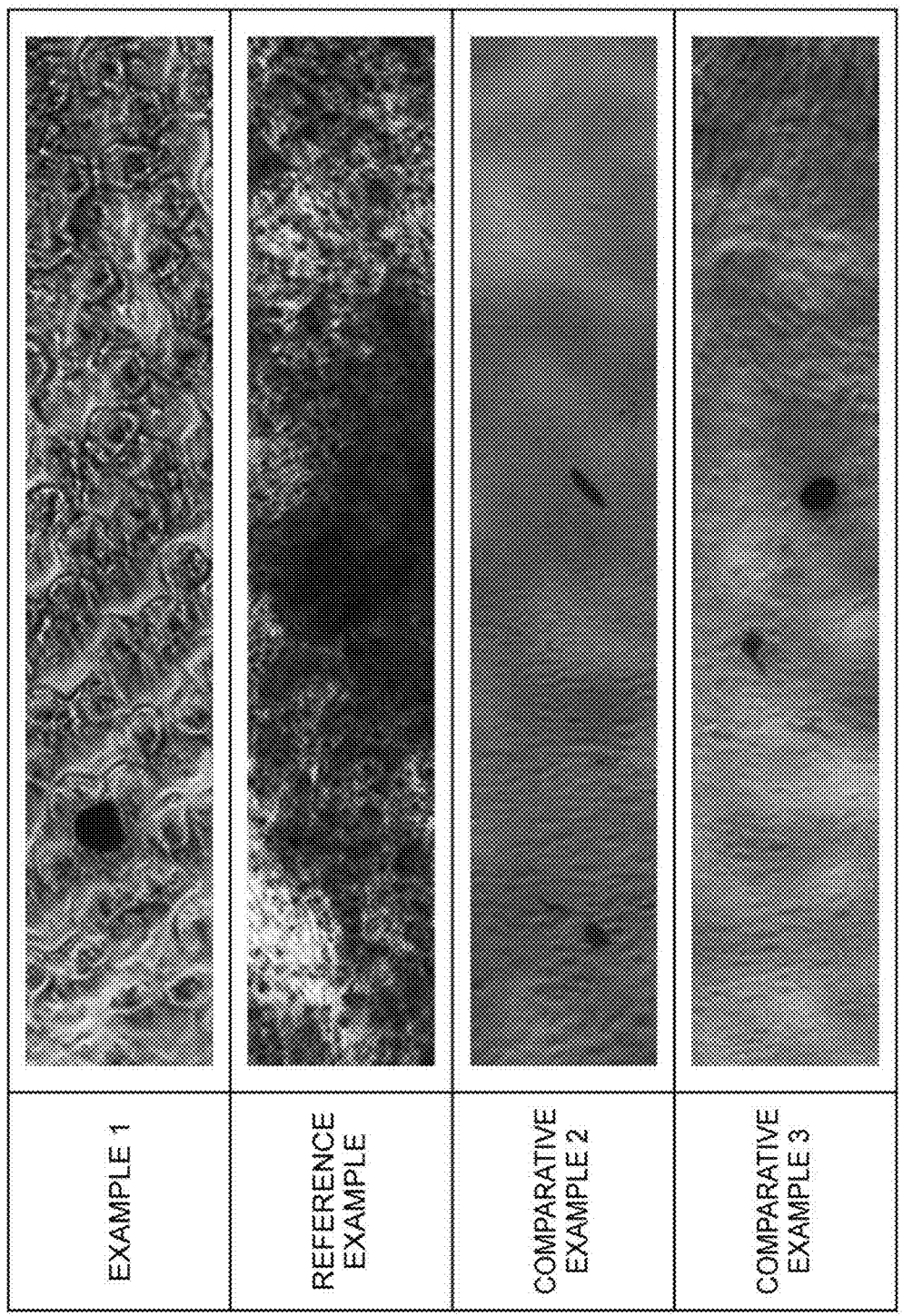
FIG. 13 is a diagram showing the results of subjecting stem cells to the induction of differentiation on a culture substrate.

FIG. 13 is a diagram showing the results of applying bone differentiation induction to stem cells on a culture substrate. In order to evaluate the terminal bone differentiation ability, staining using Alizarin Red S was carried out. As shown in FIG. 13, it can be verified that as compared to the hMSC in culture on the culture substrates of Comparative Example 2 and Comparative Example 3, the hMSC in culture on the patterned gel substrate (culture substrate) of Example 1 had a low alizarin staining intensity and was hardly stained. From this, it could be verified that the hMSC in culture on the culture substrate of Example 1 did not undergo terminal bone differentiation. On the other hand, it can be verified that the hMSC in culture on the plastic Petri dish for cell culture of Reference Example had a high alizarin staining intensity and was strongly stained. From this, it was verified that in the hMSC in culture on the plastic Petri dish for cell culture of Reference Example, normal bone differentiation induction occurred. As described above, it was verified that during culture using the culture substrate of Example 1, differentiation of hMSC is reliably suppressed.

<Evaluation of Differentiation Ability of Stem Cells after Culture Using Various Culture Substrates>

FIG. 14 is a diagram showing the results of applying differentiation induction to stem cells collected after culture. FIG. 15 is a graph showing the results of applying differentiation induction to stem cells collected after culture.

Incidentally, in FIG. 14 and FIG. 15, hMSC that had been used for culture and was subjected to bone differentiation induction is indicated as "target+", and hMSC that had been used for culture (hMSC that was not subjected to bone differentiation induction) itself is indicated as "target –". FIG. 15 is a graph produced by measuring the alizarin staining intensity (corresponding to bone differentiation induction intensity) for the samples shown in FIG. 14 as targets. As shown in FIG. 14 and FIG. 15, it was verified that the hMSC cultured on the patterned gel substrate of Example 1 and collected expressed the differentiation ability for bone differentiation induction most strongly. As described above, with regard to the culture of hMSC on the patterned gel substrate of Example 1, it was verified that hMSC exhibits resistance to differentiation induction during the culturing period, and after being collected after culture, hMSC exhibits a strong differentiation ability.

<Features of Gene Expression of Stem Cells after Culture Using Various Culture Substrates>

Human mesenchymal stem cells (hMSC) were cultured using the patterned gel substrate obtained in Example 1, and a comprehensive gene expression analysis was performed for the hMSC collected after culture as a target. hMSC was cultured for 4 days on the patterned gel substrate, and then mRNA expression was comprehensively measured using Affymetrix GeneChip Human Genome U133 Plus 2.0 Array. From the results, among the genes with enhanced expression, for twenty genes as counted from the gene with most enhanced expression to the gene having the $20^{th}$ degree of renewal of expression, the positions on the chromosome of each of the twenty genes were investigated using a gene database (UNIVERSITY of CALIFORNIA, SANTA CRUZ, Genomics Institute). The results are shown in FIG. 16.

Figure 16:
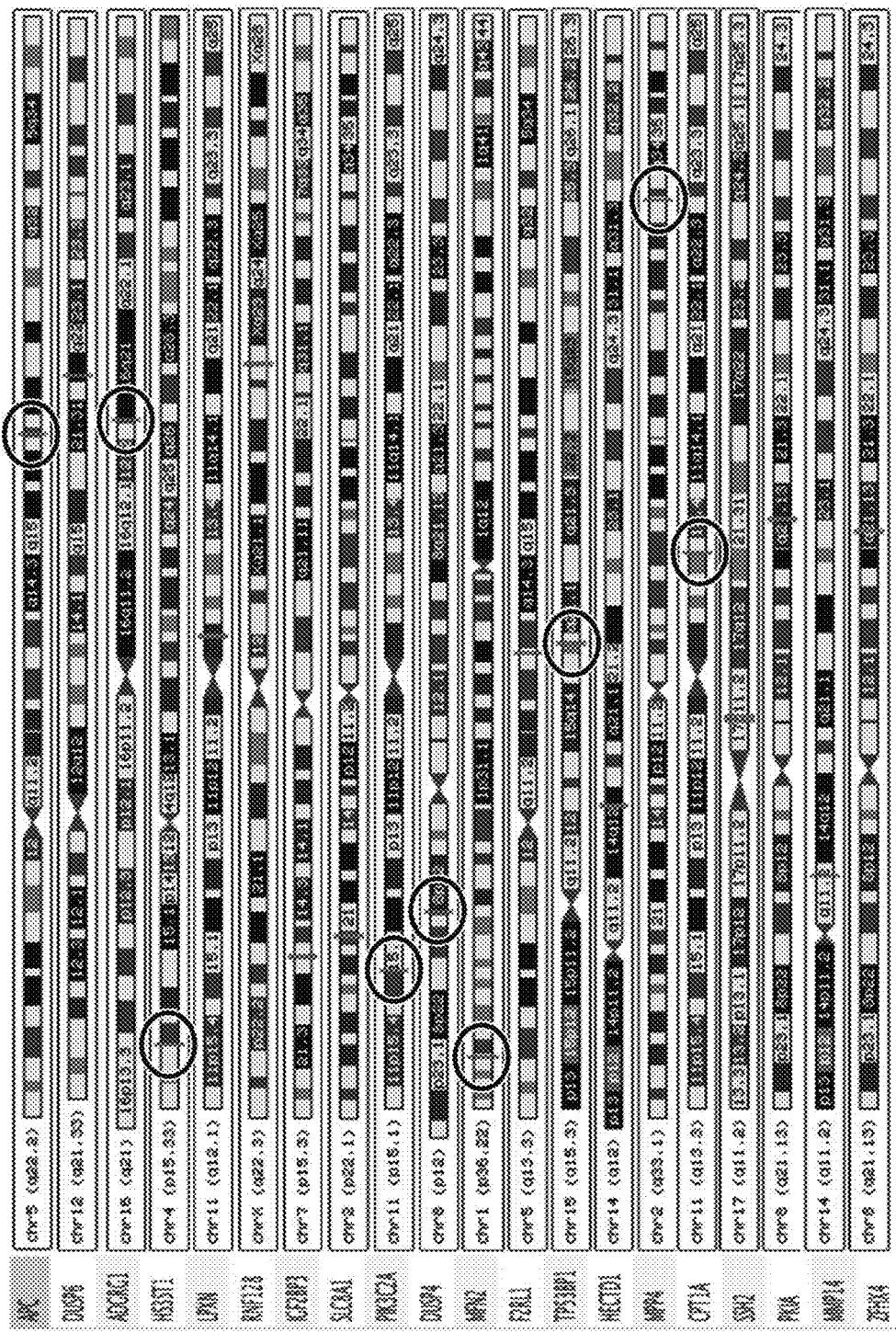
FIG. 16 is a diagram showing the positions of activated genes in stem cells that have been collected after culture.

FIG. 16 is a diagram showing the positions of activated genes in the stem cells collected after culture. FIG. 16 shows that with regard to the results of a comprehensive gene expression analysis, genes whose expression is enhanced as compared to hMSC before culture are specified, and at which positions on the gene map the genes will exist are indicated by putting in vertical lines. The gene map was obtained from the gene database. In FIG. 16, as shown by particularly assigning circle marks, as a result of a comprehensive gene analysis, it was verified that a significant number of genes whose expression was confirmed to be enhanced were located near the boundaries of the chromosome bands.

<Evaluation of Culturing Performance: Observation of Stem Cell Density>

Culture of hMSC was carried out using the culture substrates obtained in Example 1, Comparative Example 2, and Comparative Example 3 and the plastic Petri dish for cell culture of Reference Example, and the relationship between the culturing time and the cell density of stem cells on the culture substrate was evaluated. hMSC was seeded on the culture substrates or the plastic Petri dish for cell culture, and by taking the cell density of 3,000 cells/cm² after a lapse of one day after seeding as a reference, the cell densities after 2 days, after 3 days, after 4 days, and after 5 days were measured to calculate the increase rates. The cell density of the stem cells was carried out by observing with an optical microscope. The results are shown in FIG. 17 and FIG. 18.

Figure 17:
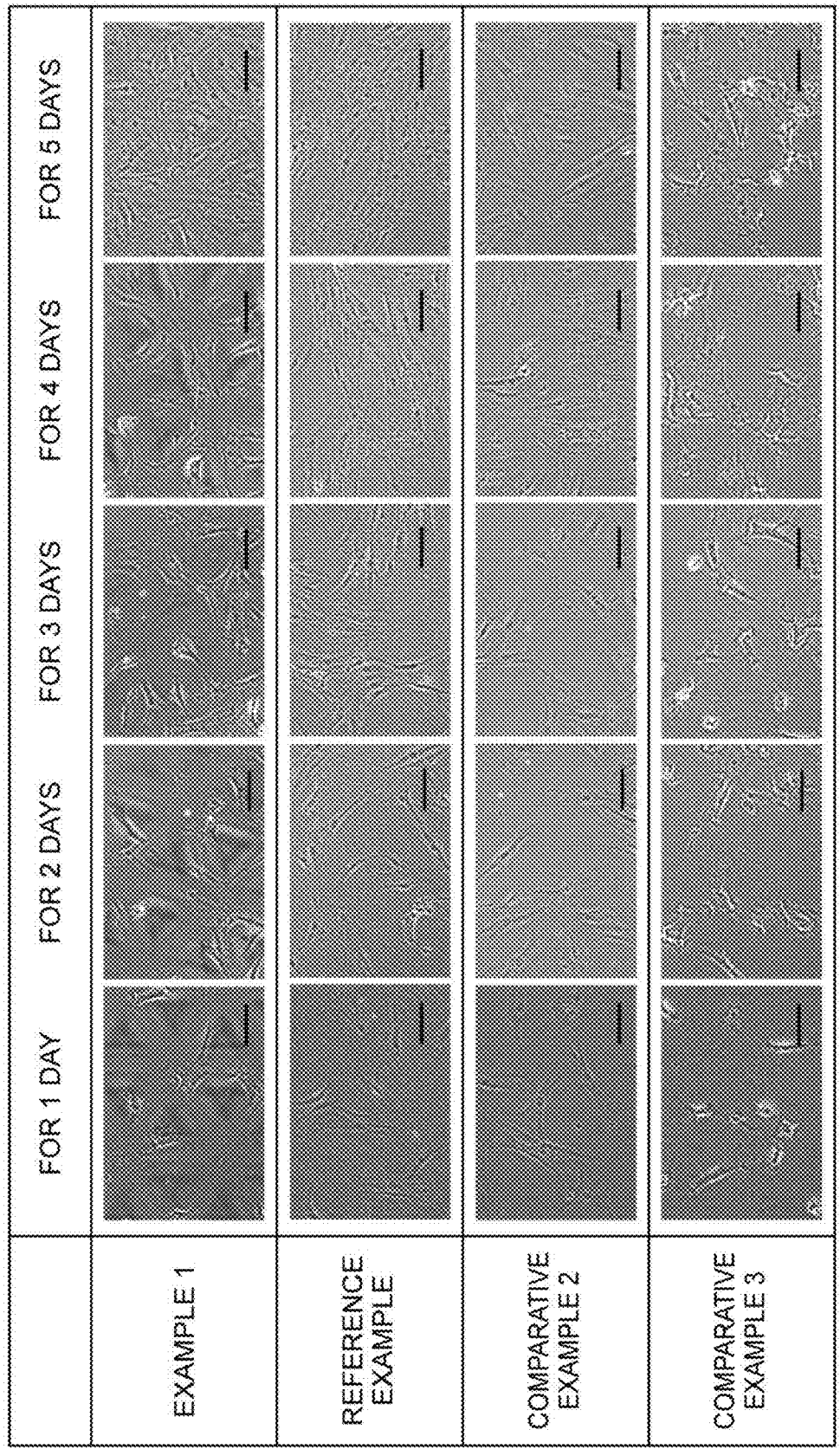
FIG. 17 is a diagram showing the relationship between the culturing time and the cell density of stem cells on a culture substrate.

FIG. 17 is a diagram showing the relationship between the culturing time and the cell density of the stem cells on the culture substrate. FIG. 17 was obtained by capturing images of some regions of the culture substrates during observation with an optical microscope. In the photographs showing the results of Example 1 in FIG. 17, the pattern formed on the culture substrate (triangular-shaped stiff regions) can be recognized in the early stage.

Figure 18:
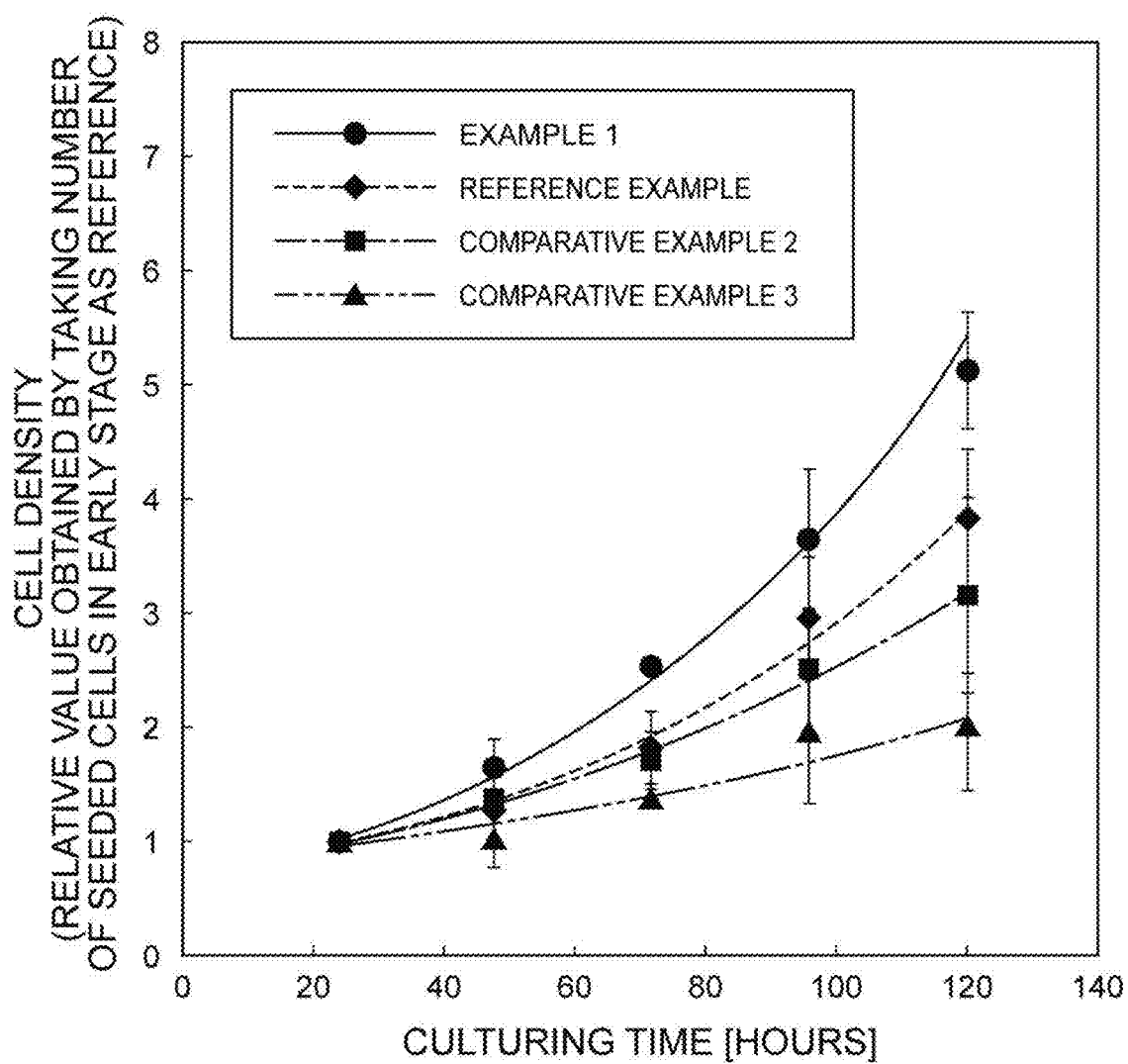
FIG. 18 is a diagram showing the relationship between the culturing time and the cell density of stem cells on a culture substrate.

FIG. 18 is a graph showing the relationship between the culturing time and the cell density of stem cells on the culture substrate. As shown in FIG. 18, it was verified that the increase rate of hMSC in the culture performed using the patterned gel substrate of Example 1 was larger than the increase rates of hMSC in the culture performed using the culture substrates obtained in Comparative Example 2 and Comparative Example 3 and the plastic Petri dish for cell culture of Reference Example.

<Evaluation of Motility of Cells During Culture> hMSC was cultured using the culture substrates obtained in Example 1, Comparative Example 2, and Comparative Example 3, and the motility of hMSC on the culture substrates was evaluated. Image capturing of each of the cell populations during culture was performed over time at an interval of 15 minutes using a phase contrast microscope. Image capturing was continued for 24 hours. The coordinates of individual hMSC were traced from the photographs thus obtained, the travel distance was measured, and thereby the movement velocity was calculated. The results are shown in FIG. 19.

Figure 19:
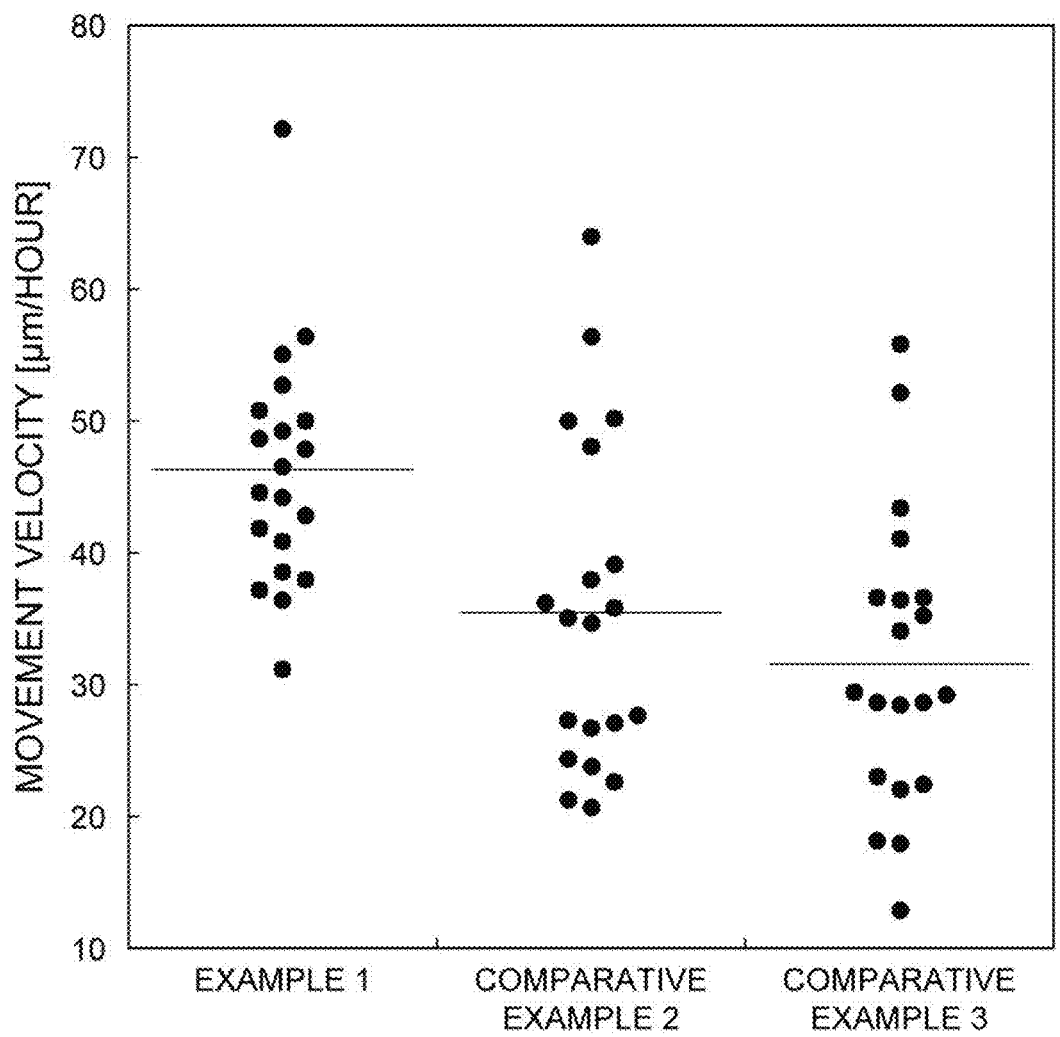
FIG. 19 is a graph showing the distribution of the movement velocity of stem cells during culture.

FIG. 19 is a graph showing the distribution of the movement velocity of stem cells during culture. Each dot on the graph represents the velocity corresponding to hMSC as an object of measurement, and the graph shows the distribution thereof. Furthermore, the straight line in the scatter plot represents the average of the distribution. It was verified that as compared to the movement velocity of hMSC on the culture substrates of Comparative Examples 2 and 3, in which there was no change in the compressive modulus of elasticity of the substrate surface, the movement velocity of hMSC on the patterned gel substrate of Example 1 was becoming faster.

INDUSTRIAL APPLICABILITY

According to the present disclosure, a culture substrate with which the direction of movement of stem cells on the substrate surface can be made isotropic, a method for manufacturing a culture substrate, and a method for culturing stem cells can be provided.

REFERENCE SIGNS LIST

10: soft region, 20: stiff region, 22: acute angle part, 50: surface, 100: culture substrate, 200, 300: photomask, 202, 302: light blocking part, 204, 304: opening, 206: apex.

The invention claimed is:
1. A culture substrate for culturing stem cells,
the culture substrate comprising a surface portion having:
  soft regions that extend side by side along a plurality of directions intersecting each other; and
  a plurality of stiff regions compartmented by the soft regions, and
  wherein in the surface portion, the stiff regions have acute angle parts protruding toward the soft regions,
  wherein a compressive modulus of the stiff regions is 30 kPa or higher and a compressive modulus of the soft regions is 10 kPa or lower,
  wherein a distance between the acute angle parts from different stiff regions is from 80 μm to 200 μm, and
  wherein a length of one side of the stiff region is from 100 μm to 300 μm, OR an area of each of the stiff regions is from 5,000 to 13,000 μm².

2. The culture substrate according to claim 1, wherein the acute angle parts exhibit a chamfering shape, and the radius of curvature thereof is 50 μm or less.

3. The culture substrate according to claim 1, wherein at least one of the plurality of stiff regions has a triangular shape.

4. The culture substrate according to claim 1, wherein the area of each of the stiff regions is 5,000 to 13,000 μm$^2$.

5. The culture substrate according to claim 1, wherein the compressive modulus of elasticity of the stiff regions is 10 or more times the compressive modulus of elasticity of the soft regions.

6. The culture substrate according to claim 1, wherein the soft regions include a photopolymerizable compound.

7. The culture substrate according to claim 6, wherein the photopolymerizable compound includes a photocurable styrenated gelatin.

8. The culture substrate according to claim 1, wherein the stiff regions have a higher coefficient of viscosity than the soft regions.

9. The culture substrate according to claim 8, wherein the acute angle parts exhibit a chamfering shape, and the radius of curvature thereof is 50 μm or less.

10. The culture substrate according to claim 8, wherein at least one of the plurality of stiff regions has a triangular shape.

11. The culture substrate according to claim 1, wherein the compressive modulus of elasticity of the stiff regions is 15 or more times the compressive modulus of elasticity of the soft regions.

12. The culture substrate according to claim 1, wherein at least one of the plurality of stiff regions has a parallelogram, rhombic or star shape.

13. The culture substrate according to claim 1, wherein the length of one side of the stiff region is from 100 μm to 300 μm.

14. A method for manufacturing a culture substrate, the method comprising:
    forming a composition layer including a photopolymerizable compound and a photopolymerization initiator, on a support; and
    irradiating the composition layer with light in a pattern-wise fashion and thereby obtaining the culture substrate according to claim 1.

15. The method for manufacturing a culture substrate according to claim 14, wherein the photopolymerizable compound includes a photocurable styrenated gelatin.

16. A method for culturing stem cells, the method comprising, culturing stem cells on the culture substrate according to claim 1.

17. A culturing device comprising stem cells and the culture substrate according to claim 1.

18. The culturing device according to claim 17, wherein the stiff regions have a higher coefficient of viscosity than the soft regions.

* * * * *